(12) United States Patent
Ghidini et al.

(10) Patent No.: US 8,835,412 B2
(45) Date of Patent: Sep. 16, 2014

(54) ISOXAZOLIDINE DERIVATIVES

(75) Inventors: Eleonora Ghidini, Parma (IT); Anna Maria Capelli, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 314 days.

(21) Appl. No.: 13/421,128

(22) Filed: Mar. 15, 2012

(65) Prior Publication Data

US 2012/0238531 A1  Sep. 20, 2012

(30) Foreign Application Priority Data

Mar. 15, 2011 (EP) .................................. 11158243

(51) Int. Cl.
*A61K 31/58* (2006.01)
*C07J 71/00* (2006.01)

(52) U.S. Cl.
CPC ..................... *C07J 71/00* (2013.01)
USPC ........................... 514/176; 540/56

(58) Field of Classification Search
USPC ............................ 540/56; 514/176
See application file for complete search history.

(56) References Cited

U.S. PATENT DOCUMENTS

| 3,631,033 A | 12/1971 | Nathansohn et al. |
| 2011/0065678 A1 | 3/2011 | Armani et al. |
| 2011/0201580 A1 | 8/2011 | Ghidini et al. |

FOREIGN PATENT DOCUMENTS

| WO | 2005/028495 | 3/2005 |
| WO | 2006/005611 | 1/2006 |
| WO | 2009/069032 | 6/2009 |
| WO | 2011/029547 | 3/2011 |

OTHER PUBLICATIONS

U.S. Appl. No. 13/421,150, filed Mar. 15, 2012, Ghidini, et al.
U.S. Appl. No. 13/964,298, filed Aug. 12, 2013, Ghidini.
European Search Report issued in European Patent Application No. 11158243.3, on Aug. 23, 2011.
Green M. J. et al., "Journal of Medicinal Chemistry, American Chemical Society", vol. 25, No. 12, (1982), pp. 1492-1495.
U.S. Appl. No. 13/561,134, filed Jul. 30, 2012, Ghidini, et al.

*Primary Examiner* — Barbara P Badio
(74) *Attorney, Agent, or Firm* — Oblon, Spivak, McClelland, Maier & Neustadt, L.L.P.

(57) ABSTRACT

Anti-inflammatory and antiallergic compounds of the glucocorticosteroid series according to formula (I) defined herein are useful for treating diseases of the respiratory tract characterized by airway obstruction.

20 Claims, No Drawings

ISOXAZOLIDINE DERIVATIVES

CROSS REFERENCES TO RELATED APPLICATIONS

This application claims priority to European Patent Application No. 11158243.3, filed on Mar. 15, 2011, which is incorporated herein by reference in its entirety.

BACKGROUND OF THE INVENTION

1. Field of the Invention

The present invention relates to novel anti-inflammatory and antiallergic compounds of the glucocorticosteroid series, methods of preparing such compounds, pharmaceutical compositions which contain such a compound, combinations which contain such a compound, and therapeutic uses thereof. The present invention also relates to methods of treating and/or preventing certain diseases and conditions by administering such a compound. More particularly, the invention relates to glucocorticosteroids that are isoxazolidine derivatives.

2. Discussion of the Background

Corticosteroids are potent anti-inflammatory agents, able to decrease the number, activity and movement of inflammatory cells. They are commonly used to treat a wide range of chronic and acute inflammatory conditions including asthma, chronic obstructive pulmonary disease (COPD), allergic rhinitis, rheumatoid arthritis, inflammatory bowel disease and autoimmune diseases. Corticosteroids mediate their effects through the glucocorticoid receptor (GR). The binding of corticosteroids to GR induces its nuclear translocation which, in turn, affects a number of downstream pathways via DNA-binding-dependent (e.g. transactivation) and -independent (e.g. transespression) mechanisms.

Corticosteroids for treating chronic inflammatory conditions in the lung such as asthma and COPD are currently administered through inhalation. One of the advantages of employing inhaled corticosteroids (ICS) is the possibility of delivering the drug directly at site of action, limiting systemic side-effects, thus resulting in a more rapid clinical response and a higher therapeutic ratio.

Although ICS treatment can afford important benefits, especially in asthma, it is important to minimize ICS systemic exposure which leads to the occurrence and severity of unwanted side effects that may be associated with chronic administration. Moreover, the limited duration of action of ICS currently available in the clinical practice contributes to suboptimal management of the disease. While the inhaler technology is the key point to target the lung, the modulation of the substituents on the corticosteroids molecular scaffold is important for the optimization of pharmacokinetic and pharmacodynamic properties in order to decrease oral bioavailability, confine pharmacological activity only in the lung (prodrugs and soft drugs), and increase systemic clearance. Moreover, long lasting ICS activity in the lung is highly desirable as once daily administration of ICS would allow the reduction of the frequency of administration and, thus, substantially improve patient compliance and, as a result, disease management and control. In sum, there is a pressing medical need for developing ICS with improved pharmacokinetic and pharmacodynamic characteristics.

Glucocorticoids isoxazolidine derivatives are for instance described in WO 2006/005611, GB 1578446, and in "Synthesis and topical anti-inflammatory activity of some steroidal [16α,17α-d] isoxazolidines" (J. Med. Chem., 25, 1492-1495, 1982), all of which are incorporated herein by reference in their entireties. Some glucocorticoids isoxazolidine derivatives are also described in the co-pending patent application WO2011/029547, which is incorporated herein by reference in its entirety.

Thus, there remains a need for ICS with improved pharmacokinetic and pharmacodynamic characteristics.

SUMMARY OF THE INVENTION

Accordingly, it is one object of the present invention to provide novel anti-inflammatory and antiallergic compounds.

It is another object of the present invention to provide novel anti-inflammatory and antiallergic compounds, with improved pharmacokinetic and pharmacodynamic characteristics.

It is another object of the present invention to provide novel anti-inflammatory and antiallergic compounds of the glucocorticosteroid series.

It is another object of the present invention to provide novel methods of preparing such a compound.

It is another object of the present invention to provide novel pharmaceutical compositions which contain such a compound.

It is another object of the present invention to provide novel combinations of such a compound and another active agent.

It is another object of the present invention to provide novel therapeutic uses of such a compound.

It is another object of the present invention to provide novel methods of treating and/or preventing certain diseases and conditions by administering such a compound.

These and other objects, which will become apparent during the following detailed description, have been achieved by the inventors' discovery that compounds of formula (I), described below, exhibit improved developability, and pharmacokinetic and pharmacodynamic characteristics, such as low systemic exposure, great selectivity, potency or duration of action.

Thus, the present invention provides anti-inflammatory and antiallergic compounds of the glucocorticosteroid series of formula (I).

In another embodiment, the present invention provides to processes for preparing a compound of formula (I).

In another embodiment, the present invention provides pharmaceutical compositions which contain a compound of formula (I).

In another embodiment, the present invention provides combinations of a compound of formula (I) with other pharmaceutical active ingredients for the treatment of respiratory disorders, among which beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs) and mucus regulators.

In another embodiment, the present invention provides methods of treating and/or preventing certain diseases by administering a compound of formula (I).

Surprisingly, it has been found that the compounds of the present invention show improved developability, pharmacokinetic or pharmacodynamic characteristics, such as low systemic exposure, great selectivity, potency or duration of action.

DETAILED DESCRIPTION OF THE PREFERRED EMBODIMENTS

In particular, the invention is directed to compounds of general formula (I):

(I)

wherein
$R_1$ is $(CH_2)_n$—Z—$(CH_2)_{n'}$—R4
n is 0, 1 or 2;
n' is 0, 1 or 2;
Z is a single bond or is selected from the group consisting of —S—, —O—, —C(O)— and —NR$_3$—;
$R_3$ is selected from the group consisting of H, $(C_1-C_6)$alkyl, $(C_1-C_6)$haloalkyl, $(C_3-C_8)$cycloalkyl, aryl, aryl$(C_1-C_6)$alkyl and heteroaryl, which are optionally substituted by —CN;
$R_4$ is selected from the groups consisting of:
  H, halogen, —OH, —SH, —CN and —NR$_6$R$_7$;
  aryl$(C_1-C_6)$alkyl, $(C_1-C_6)$alkylsulfonyl, $(C_1-C_6)$alkylcarbonyl, $(C_1-C_6)$alkylcarboxyl, HO$(C_1-C_6)$alkylcarboxyl, $(C_1-C_6)$alkylamide, and $(C_1-C_6)$alkoxy, which are optionally substituted by oxo groups;
  $(C_1-C_6)$alkyl which may be optionally substituted by one or more substituents selected from the group consisting of halogen atoms, —CN, —OH, —NH$_2$, —NO$_2$, —CF$_3$, and —SH;
  $(C_2-C_6)$alkynyl;
  $(C_5-C_{17})$alkenylcarbonyl; and
  a mono-, bi- or tricyclic saturated or partially unsaturated or unsaturated ring, such as $(C_3-C_8)$cycloalkyl, aryl, $(C_5-C_{10})$heterocycloalkyl, or heteroaryl, optionally substituted by one or more halogen atoms or oxo groups;
$R_6$ and $R_7$ are independently selected from the group consisting of H, $(C_1-C_6)$alkyl, and $(C_1-C_6)$alkoxy;
X and Y are independently H or halogen atoms;
$R_2$ is selected from the group consisting of: —$(CH_2)_s$—K-A-$(CH_2)_t$—W, —$(CH_2)_s$—K—$(CH_2)_t$—B—W, and —$(CH_2)_s$—$(CHR_5)$—W;
s is 0 or 1;
t is 0 or 1;
K is selected from the group consisting of: a group —CH=CH—, arylene, and heteroarylene, where such arylene and heteroarylene groups may be optionally substituted by one or more groups independently selected from: halogen, $(C_1-C_6)$alkyl, —OH, $(C_1-C_6)$alkoxy, and $(C_1-C_6)$haloalkyl;
A is selected from the group consisting of: a bond, a group —O— and a group —S—;
B is selected from the group consisting of: a bond, a group —O— and a group —S—;
W is aryl or heteroaryl, where such aryl and heteroaryl groups may be optionally substituted by one or more groups independently selected from: halogen, —OH, $(C_1-C_6)$alkyl, $(C_1-C_6)$alkoxy, and $(C_1-C_6)$haloalkyl;
$R_5$ is aryl or heteroaryl, where such aryl and heteroaryl groups may be optionally substituted by one or more groups independently selected from: halogen, $(C_1-C_6)$alkyl, $(C_1-C_6)$alkoxy, —OH, and $(C_1-C_6)$haloalkyl;
and pharmaceutically acceptable salts thereof;
with the proviso that for compounds of formula (I) when s is 1, K is optionally substituted heteroarylene, t is zero and A or B is a bond, then W is optionally substituted heteroaryl.

In another embodiment, compounds of formula (IA) are provided (IA)

wherein
$R_1$ is $(CH_2)_n$—Z—$(CH_2)_{n'}$—R4
n is 0, 1 or 2;
n' is 0, 1 or 2;
Z is a single bond or is selected from the group consisting of —S—, —O—, —C(O)—, and —NR$_3$—;
$R_3$ is selected from the group consisting of H, $(C_1-C_6)$alkyl, $(C_1-C_6)$haloalkyl, $(C_3-C_8)$cycloalkyl, aryl, aryl$(C_1-C_6)$alkyl, and heteroaryl, which are optionally substituted by —CN;
$R_4$ is selected from the groups consisting of:
  H, halogen, —OH, —SH, —CN and —NR$_6$R$_7$;
  aryl$(C_1-C_6)$alkyl, $(C_1-C_6)$alkylsulfonyl, $(C_1-C_6)$alkylcarbonyl, $(C_1-C_6)$alkylcarboxyl, HO$(C_1-C_6)$alkylcarboxyl, $(C_1-C_6)$alkylamide, and $(C_1-C_6)$alkoxy, which are optionally substituted by oxo groups;
  $(C_1-C_6)$alkyl which may be optionally substituted by one or more substituents selected from the group consisting of halogen atoms, —CN, —OH, —NH$_2$, —NO$_2$, —CF$_3$, and —SH;
  $(C_2-C_6)$alkynyl;
  $(C_5-C_{17})$alkenylcarbonyl; and
  a mono-, bi- or tricyclic saturated or partially unsaturated or unsaturated ring, such as $(C_3-C_8)$cycloalkyl, aryl, $(C_5-C_{10})$heterocycloalkyl, or heteroaryl, optionally substituted by one or more halogen atoms or oxo groups;
$R_6$ and $R_7$ are independently selected from the group consisting of H, $(C_1-C_6)$alkyl and $(C_1-C_6)$alkoxy;
X and Y are independently H or halogen atoms;
$R_2$ is selected from the group consisting of: —$(CH_2)_s$—K-A-$(CH_2)_t$—W, —$(CH_2)_s$—K—$(CH_2)_t$—B—W, and —$(CH_2)_s$—$(CHR_5)$—W;
s is 0 or 1;
t is 0 or 1;
K is selected from the group consisting of: a group —CH=CH—, arylene, and heteroarylene, where such arylene and heteroarylene groups may be optionally substituted by one or more groups independently selected from: halogen, $(C_1\text{-}C_6)$alkyl, —OH, $(C_1\text{-}C_6)$ alkoxy, and $(C_1\text{-}C_6)$haloalkyl;

A is selected from the group consisting of: a bond, a group —O— and a group —S—;

B is selected from the group consisting of: a bond, a group —O— and a group —S—;

W is aryl or heteroaryl, where such aryl and heteroaryl groups may be optionally substituted by one or more groups independently selected from: halogen, —OH, $(C_1\text{-}C_6)$alkyl, $(C_1\text{-}C_6)$alkoxy, and $(C_1\text{-}C_6)$haloalkyl;

$R_5$ is aryl or heteroaryl, where such aryl and heteroaryl groups may be optionally substituted by one or more groups independently selected from: halogen, $(C_1\text{-}C_6)$ alkyl, $(C_1\text{-}C_6)$alkoxy, —OH, and $(C_1\text{-}C_6)$haloalkyl;

and pharmaceutically acceptable salts thereof;

with the proviso that the compound of formula (IA) is not:
(4aS,4bR,5S,6aS,6bR,9aS,10aS,10bS,12S)-4b,12-Difluoro-5-hydroxy-6b-(2-hydroxy-acetyl)-4a,6a-dimethyl-8-(2-phenyl-thiazol-4-ylmethyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,1S)-4b,12-Difluoro-5-hydroxy-6b-(2-hydroxy-acetyl)-4a,6a-dimethyl-8-(5-phenyl-furan-2-ylmethyl)-4a,4b,5,6,6a,6b,8,9,9a,10,10a,10b,11,12-tetradecahydro-7-oxa-8-aza-pentaleno[2,1-a]phenanthren-2-one; or (4aS,4bR,5S,6aS,6bR,9aS,10aS,10bS,12S)-4b,12-Difluoro-5-hydroxy-6b-(2-hydroxy-acetyl)-4a,6a-dimethyl-8-(5-phenyl-isoxazol-3-ylmethyl)-4a,4b,5,6,6a,6b,8,9,9a,10,10a,10b,11,12-tetradecahydro-7-oxa-8-aza-pentaleno[2,1-a]phenanthren-2-one.

In the present description, unless otherwise provided, the term "halogen" includes fluorine, chlorine, bromine and iodine atoms.

The term "$(C_1\text{-}C_6)$alkyl" refers to straight or branched chain alkyl groups wherein the number of carbon atoms is from 1 to 6. Examples of said groups are methyl, ethyl, n-propyl, isopropyl, n-butyl, isobutyl, sec-butyl, tert-butyl, pentyl, hexyl, and the like.

The expression "$(C_1\text{-}C_6)$alkylcarboxyl" refers to alkyl-COO groups.

The expression "$(C_1\text{-}C_6)$alkylcarbonyl" refers to —$(C_1\text{-}C_6)$alkyl CO— groups.

The expression "$(C_1\text{-}C_6)$alkylamide" refers to —C(O)—NH—$(C_1\text{-}C_6)$alkyl groups.

The term "$(C_5\text{-}C_{17})$alkenyl" refers to straight or branched, conjugated or non-conjugated, carbon chains with one or more double bonds, in cis or trans configuration, wherein the number atoms is in the range 5 to 17.

Examples of said groups are trans octadec-9-enyl, cis 9-octadec-9-enyl, cis,cis-9,12-octadecadienyl, and hexadec-9-enyl.

The expression "$(C_5\text{-}C_{17})$alkenylcarbonyl" refers to $(C_5\text{-}C_{17})$alkenyl-CO— groups.

The term "$(C_2\text{-}C_6)$alkynyl" refers to straight or branched carbon chains with one or more triple bonds wherein the number atoms is in the range 2 to 6.

The term "$(C_1\text{-}C_6)$alkoxy" refers to alkyl-oxy (e.g. alkoxy) groups, with the alkyl portion as above defined. Examples of said groups may thus comprise methoxy, ethoxy, n-propoxy, isopropoxy, n-butoxy, isobutoxy, sec-butoxy, tert-butoxy, pentoxy, hexoxy, and the like.

The expressions "$(C_1\text{-}C_6)$alkoxycarbonyl" and "hydroxy $(C_1\text{-}C_6)$ alkoxy" refer respectively to alkoxy-CO— and (OH) alkoxy-groups.

The expressions "$(C_1\text{-}C_6)$haloalkyl" and "$(C_1\text{-}C_6)$haloalkoxy" refer to the above "$(C_1\text{-}C_6)$alkyl" and "$(C_1\text{-}C_6)$ alkoxy" groups wherein one or more hydrogen atoms are replaced by one or more halogen atoms, which can be the same or different from each other.

Examples of said $(C_1\text{-}C_6)$haloalkyl and $(C_1\text{-}C_6)$haloalkoxy groups may thus include halogenated, poly-halogenated, and fully halogenated alkyl and alkoxy groups wherein all of the hydrogen atoms are replaced by halogen atoms, e.g. trifluoromethyl or trifluoromethoxyl groups.

The expression "$(C_3\text{-}C_8)$cycloalkyl" refers to mono- or bi-cycloaliphatic hydrocarbon groups with from 3 to 8 carbon atoms. Examples include cyclopropyl, cyclobutyl, cyclopentyl, cyclohexyl, cycloheptyl, and the like.

The expression "$(C_5\text{-}C_{10})$heterocycloalkyl" refers to $(C_5\text{-}C_{10})$cycloalkyl groups, in which at least one ring carbon atom is replaced by a heteroatom or heteroaromatic group (e.g. N, NH, S or O).

The expression "aryl" refers to mono- or bi- or tri-cyclic ring radicals which have 6 to 20 ring atoms, preferably from 6 to 15, and wherein at least one ring is aromatic.

The expressions "aryloxy" and "arylthio" refer respectively to aryl-oxy and aryl-S— groups, with the aryl portion as above defined.

The term "aryl$(C_1\text{-}C_6)$alkyl" refers to a "$(C_1\text{-}C_6)$alkyl" groups as above defined wherein one of the hydrogen atoms is replaced by an "aryl" group as above defined. Examples include a benzyl group.

The expression "$(C_1\text{-}C_6)$alkylsulfonyl" refer to alkyl-$SO_2$— groups.

The expression "heteroaryl" refers to mono-, bi- or tri-cyclic ring radicals with 5 to 20 ring atoms, preferably from 5 to 15, in which at least one ring is aromatic and in which at least one carbon ring atom is a heteroatom or heteroaromatic group (e.g. N, NH, S or O).

Examples of suitable aryl or heteroaryl monocyclic systems include, for instance, thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolinyl), furan (furanyl) radicals, and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinoline (quinolinyl), isoquinoline (isoquinolinyl), indole (indolyl), isoindole (isoindolyl), benzothiophene (benzothiophenyl), dihydrobenzo dioxin, dihydrobenzo dioxepine, benzo oxazine radicals, and the like.

Examples of suitable aryl or heteroaryl tricyclic systems include fluorene (fluorenyl) radicals as well as benzo-condensed derivatives of the aforementioned heteroaryl bicyclic systems.

By analogy, the expressions "arylene" and "heteroarylene" refer to a divalent aryl (such as for example phenylene) or heteroaryl radical, wherein aryl and heteroaryl groups are as above defined.

It will be apparent to those skilled in the art that compounds of general formula (I) contain asymmetric centers at least at the positions 4a, 4b, 5, 6a, 6b, 9a, 10a, 10b, and therefore may exist as many optical stereoisomers and mixtures thereof. Therefore the invention is also directed to all of these forms and mixtures thereof.

Preferred compounds are those of general formula (I) wherein the stereochemistry of stereogenic carbon atoms is as reported in formula (I') hereinbelow and wherein the meanings of $R_1$ and $R_2$, X, and Y are as defined above for compounds of formula (I):

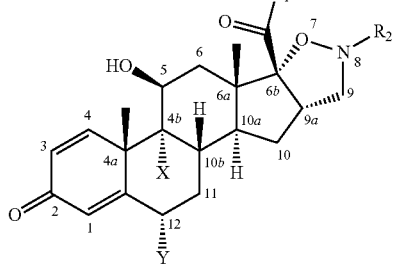

(I')

Also, preferred compounds are those of general formula (IA) wherein the stereochemistry of stereogenic carbon atoms is as reported in formula (IA') hereinbelow and wherein the meanings of $R_1$ and $R_2$, X, and Y are as defined above for compounds of formula (IA):

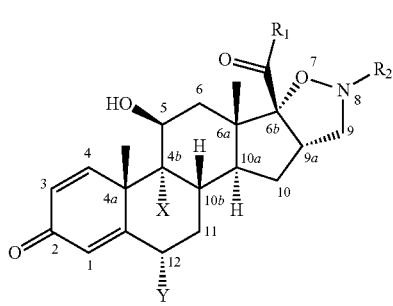

(IA')

The absolute configuration is assigned on the basis of Cahn-Ingold-Prelog nomenclature based on groups' priorities.

In one preferred embodiment, in the compounds of formula (I') or (IA'), the absolute configuration at asymmetric center 4a is (S), at 4b is (R), at 5 is (S), at 6a is (S), at 6b is (R), at 9a is (S), at 10a is (S), at 10b is (S) and at 12 is (S).

Compounds of general formula (I) or (IA) may form acid or basic addition salts, particularly pharmaceutically acceptable salts.

Pharmaceutically acceptable acid addition salts of the compounds of formula (I) or (IA), thus encompassing also those of formula (I') or (IA'), include those of inorganic acids, for example hydrohalogen acids such as hydrofluoric, hydrochloric, hydrobromic or hydroiodic; nitric; sulfuric; phosphoric; and organic acids, for example aliphatic monocarboxylic acids such as formic, acetic, trifluoroacetic, and propionic; aliphatic hydroxyl acids such as lactic, citric, tartaric, or malic; dicarboxylic acids such as maleic, fumaric, oxalic, or succinic; aromatic carboxylic acids such as benzoic; aromatic hydroxyl acids; and sulfonic acids.

Pharmaceutically acceptable base addition salts refers to derivatives of compounds of formula (I) or (IA) wherein the parent compound is suitably modified by converting any free acid group, if present, to the corresponding addition salt with a suitable pharmaceutically acceptable base.

Examples of said salts may include mineral or organic base addition salts of acid residues such as carboxylic groups.

Cations of inorganic bases which can be suitably used to prepare salts within the invention comprise ions of alkali or alkaline earth metals such as potassium, sodium, calcium, or magnesium.

These salts may be prepared from compounds of formula (I), (I'), (IA), or (IA') by known salt-forming procedures.

It is to be understood that all preferred groups or embodiments described hereinbelow for compounds of formula (I) may be combined among each other and apply to compounds of formula (IA), (I)', (IA'), (IB), (IC), (ID), (IE), (IF) as well mutatis mutandis.

In a preferred embodiment, in the compounds of formula (I), at least one of X and Y is a halogen atom. In a more preferred embodiment, both X and Y are a halogen atom. In a still more preferred embodiment, both X and Y are fluorine.

In a preferred embodiment, in the compounds of formula (I), $R_1$ is $—(CH_2)_n—Z—(CH_2)_{n'}—R_4$, wherein n is 1, Z is a single bond, n' is 0, and $R_4$ is a group —OH, or $R_1$ is $—(CH_2)_n—Z—(CH_2)_{n'}—R_4$, wherein n is 0, Z is —S—, n' is 1, and $R_4$ is a halogen atom, or $R_1$ is $—(CH_2)_n—Z—(CH_2)_{n'}—R_4$, wherein n is 0, Z is a bond, n' is 1, and $R_4$ is a halogen atom. In a more preferred embodiment, $R_1$ is $—(CH_2)_n—Z—(CH_2)_{n'}—R_4$, wherein n is 0, Z is —S—, n' is 1, and $R_4$ is a halogen atom, or $R_1$ is $—(CH_2)_n—Z—(CH_2)_{n'}—R_4$, wherein n is 0, Z is a bond, n' is 1, and $R_4$ is a halogen atom. In a further preferred embodiment, $R_1$ is $—(CH_2)_n—Z—(CH_2)_{n'}—R_4$, wherein n is 0, Z is —S—, n' is 1, and $R_4$ is a halogen atom, or $R_1$ is $—(CH_2)_n—Z—(CH_2)_{n'}—R_4$, wherein n is 1, Z is a single bond, n' is 0, and $R_4$ is the group —OH.

Preferably, $R_1$ is $—(CH_2)_n—Z—(CH_2)_{n'}—R_4$, wherein n is 1, Z is a single bond, n' is 0, and $R_4$ is the group —OH.

In another preferred embodiment, $R_1$ is $—(CH_2)_n—Z—(CH_2)_{n'}—R_4$, wherein n is 0, Z is —S—, n' is 1, and $R_4$ is a halogen atom. Preferably the halogen atom is fluorine.

In a further preferred embodiment, $R_1$ is $—(CH_2)_n—Z—(CH_2)_{n'}—R_4$, wherein n is 0, Z is a bond, n' is 1, and $R_4$ is a halogen atom. Preferably the halogen atom is fluorine.

In a preferred embodiment, $R_2$ is a group $—(CH_2)_s—(CHR_5)—W$.

In more preferred embodiment, $R_2$ is a group $—(CH_2)_s—K-A-(CH_2)_t—W$ or a group $—(CH_2)_s—K—(CH_2)_t—B—W$.

In a preferred embodiment, in the compounds of formula (I) s is zero.

In another preferred embodiment, in the compounds of formula (I) s is 1.

In a preferred embodiment, K is a group —CH=CH—. In a more preferred embodiment, K is optionally substituted arylene or heteroarylene.

In a preferred embodiment, in the compounds of formula (I), $R_2$ is selected from the group consisting of: $—(CH_2)_s—K-A-(CH_2)_t—W$ or $—(CH_2)_s—K—(CH_2)_t—B—W$; s is 0 or 1; K is optionally substituted arylene or heteroarylene; A is selected from the group consisting of: a bond, a group —O— and a group —S—; B is selected from the group consisting of: a bond, a group —O— and a group —S—; t is 0 or 1; and W is optionally substituted aryl or heteroaryl.

In another preferred embodiment, in the compounds of formula (I), $R_2$ is selected from the group consisting of: $—(CH_2)_s—K-A-(CH_2)_t—W$ or $—(CH_2)_s—K—(CH_2)_t—B—W$; s is 0 or 1; K is optionally substituted arylene or heteroarylene; A is selected from the group consisting of: a bond, a group —O— and a group —S—; B is selected from the group consisting of: a bond, a group —O— and a group —S—; t is 1; and W is optionally substituted aryl or heteroaryl.

In a further embodiment, in the compounds of formula (I), $R_2$ is selected from the group consisting of: $—(CH_2)_s—K-A-(CH_2)_t—W$ or $—(CH_2)_s—K—(CH_2)_t—B—W$; s is 0 or 1; K is optionally substituted arylene; A is selected from the group consisting of: a bond, a group —O— and a group —S—; B is selected from the group consisting of: a bond, a group —O— and a group —S—; t is 0 or 1; and W is optionally substituted aryl or heteroaryl.

In another preferred embodiment, $R_2$ is selected from the group consisting of: —(CH$_2$)$_s$—K-A-(CH$_2$)$_t$—W or —(CH$_2$)$_s$—K—(CH$_2$)$_t$—B—W; s is 0; K is optionally substituted arylene or heteroarylene; A is selected from the group consisting of: a bond, a group —O— and a group —S—; B is selected from the group consisting of: a bond, a group —O— and a group —S—; t is 0 or 1; and W is optionally substituted aryl or heteroaryl.

In further preferred embodiment, $R_2$ is selected from the group consisting of: —(CH$_2$)$_s$—K-A-(CH$_2$)$_t$—W or —(CH$_2$)$_s$—K—(CH$_2$)$_t$—B—W; s is 1; K is optionally substituted arylene or heteroarylene; A is selected from the group consisting of: a bond, a group —O— and a group —S—; B is selected from the group consisting of: a bond, a group —O— and a group —S—; t is 0 or 1; and W is optionally substituted aryl or heteroaryl.

In another preferred embodiment, $R_2$ is selected from the group consisting of: —(CH$_2$)$_s$—K-A-(CH$_2$)$_t$—W or —(CH$_2$)$_s$—K—(CH$_2$)$_t$—B—W; s is 1; K is optionally substituted arylene; A is selected from the group consisting of: a bond, a group —O— and a group —S—; B is selected from the group consisting of: a bond, a group —O— and a group —S—; t is 0 or 1; and W is optionally substituted aryl.

In another preferred embodiment, $R_2$ is selected from the group consisting of: —(CH$_2$)$_s$—K-A-(CH$_2$)$_t$—W or —(CH$_2$)$_s$—K—(CH$_2$)$_t$—B—W; s is 1; K is optionally substituted arylene; A is selected from the group consisting of: a bond, a group —O— and a group —S—; B is selected from the group consisting of: a bond, a group —O— and a group —S—; t is 0 or 1; and W is optionally substituted heteroaryl.

In a preferred embodiment, s is zero or 1; K is optionally substituted arylene or heteroarylene; A is a group —O—; t is 0 or 1; and W is optionally substituted aryl or heteroaryl.

In another preferred embodiment, s is zero or 1; K is optionally substituted arylene or heteroarylene; B is a group —O—; t is 0 or 1; and W is optionally substituted aryl or heteroaryl.

In a preferred embodiment, in the compounds of formula (I), aryl is a phenyl ring and heteroaryl is a 5- or 6-membered monocyclic heteroaryl ring.

In another preferred embodiment, in the compounds of formula (I), aryl is a phenyl ring.

In another preferred embodiment, in the compounds of formula (I), heteroaryl is 5- or 6-membered monocyclic heteroaryl ring.

In a preferred embodiment, in the compounds of formula (I), arylene is a phenyl ring and heteroarylene is 5- or 6-membered monocyclic heteroarylene ring.

In another preferred embodiment, in the compounds of formula (I), arylene is a phenylene ring.

In another preferred embodiment, in the compounds of formula (I), heteroarylene is 5- or 6-membered monocyclic heteroarylene ring.

A preferred group of compounds of general formula (I) is that of formula (IB), wherein X and Y are fluorine, n is 0 or 1, n' is 0 or 1; Z is a single bond, a group —S— or a group —O—; R4 is selected from the groups consisting of: H, halogen, —OH, —SH, —CN, and —NR$_6$R$_7$, optionally substituted (C$_1$-C$_6$)alkylsulfonyl, optionally substituted (C$_1$-C$_6$)alkylcarbonyl, optionally substituted (C$_1$-C$_6$)alkylcarboxyl, optionally substituted (C$_1$-C$_6$)alkyl, and an optionally substituted monocyclic (C$_5$-C$_{10}$)heterocycloalkyl; and the groups $R_2$, $R_6$, and $R_7$ are as above defined for compounds of formula (I).

Another preferred group of compounds of general formula (I) is that of formula (IC), wherein X and Y are fluorine, $R_1$ is —(CH$_2$)$_n$—Z—(CH$_2$)$_{n'}$—R$_4$, wherein n is 1, Z is a single bond; n' is 0; and R4 is the group —OH

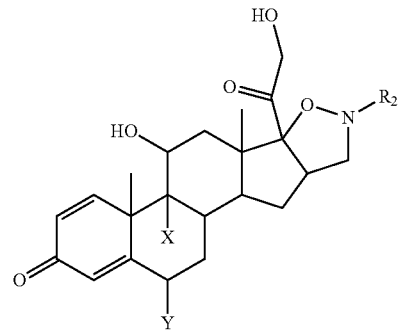

(IC)

and the group $R_2$ is as above defined for compounds of formula (I).

A further preferred group of compounds of general formula (I) is that of formula (ID), wherein X and Y are fluorine, $R_1$ is —(CH$_2$)$_n$—Z—(CH$_2$)$_{n'}$—R$_4$, wherein n is 0, Z is —S—; n' is 1; and $R_4$ is an halogen atom:

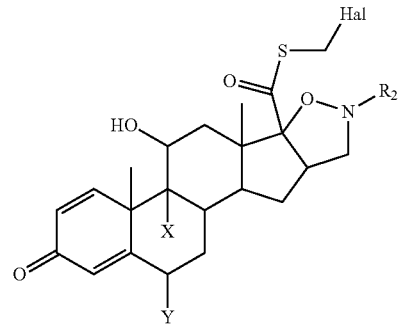

(ID)

and the group $R_2$ is as above defined for compounds of formula (I). Preferably, the halogen atom in $R_4$ is fluorine.

A further preferred group of compounds of general formula (I) is that of formula (IE), wherein X and Y are fluorine, $R_1$ is —(CH$_2$)$_n$—Z—(CH$_2$)$_{n'}$—R$_4$, wherein n is 0, Z is a bond; n' is 1; and $R_4$ is an halogen atom:

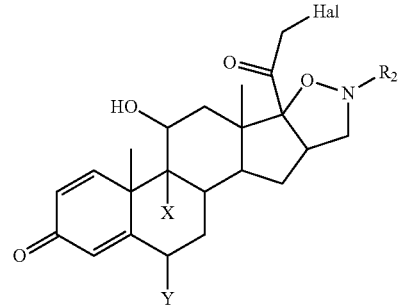

(IE)

and the group R₂ is as above defined for compounds of formula (I). Preferably, the halogen atom in R₄ is fluorine.

A preferred group of compounds of general formula (I) is that of formula (IF), wherein X and Y are fluorine, R₂ is selected from the group consisting of: —(CH₂)$_s$—K-A-(CH₂)$_t$—W or —(CH₂)$_s$—K—(CH₂)$_t$—B—W; s is 0 or 1; K is optionally substituted arylene or heteroarylene; A is selected from the group consisting of: a bond, a group —O— and a group —S—; B is selected from the group consisting of: a bond, a group —O— and a group —S—; t is 0 or 1; W is optionally substituted aryl or heteroaryl; and the group R₁ is as above defined for compounds of formula (I).

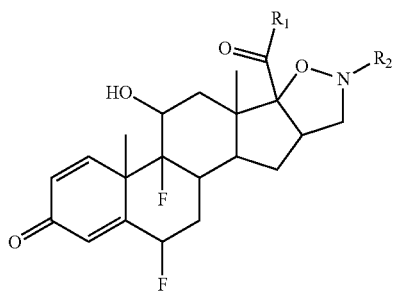

(IF)

In a preferred embodiment, for compounds of formula (IF), R₁ is —(CH₂)$_n$—Z—(CH₂)$_{n'}$—R₄, wherein n is 1, Z is a single bond; n' is 0; R₄ is the group —OH.

In another preferred embodiment, in the compounds of formula (IF), R₁ is —(CH₂)$_n$—Z—(CH₂)$_{n'}$—R₄, wherein n is 0, Z is —S—; n' is 1; and R₄ is a halogen atom.

In a further preferred embodiment, in the compounds of formula (IF), R₁ is —(CH₂)$_n$—Z—(CH₂)$_{n'}$—R₄, wherein n is 0, Z is a bond; n' is 1; and R₄ is an halogen atom.

It is to be understood that the present invention covers all combinations of particular and preferred groups and embodiments described hereinabove.

Hereinafter, compounds of formula (I), (I'), (IA), (IA') (IB), (IC), (ID), (IE), (IF) and their pharmaceutically acceptable salts (except intermediate compounds described in the chemical processes) are referred to as "compounds of the invention."

Examples of preferred compounds of the invention are:

| Compound | Chemical Name |
|---|---|
| 6 | (4aS,4bR,5S,6aS,6bR,9aS,10aS,10bS,12S)-4b,12-Difluoro-8-[4-(4-fluoro-benzyloxy)-benzyl]-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 7 | (4aS,4bR,5S,6aS,6bR,9aS,10aS,10bS,12S)-4b,12-Difluoro-8-[4-(4-fluoro-benzyloxy)-benzyl]-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 8 | (4aS,4bR,5S,6aS,6bR,9aS,10aS,10bS,12S)-8-((4-fluoro-benzyloxy)-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 12 | (4aS,4bR,5S,6aS,6bR,9aS,10aS,10bS,12S)-8-(4-Benzyloxy-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 13 | (4aS,4bR,5S,6aS,6bR,9aS,10aS,10bS,12S)-8-(4-Benzyloxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |
| 14 | (4aS,4bR,5S,6bR,9aS,10aS,10bS,12S)-8-((S)-4-Benzyloxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |

-continued

| Compound | Chemical Name |
|---|---|
| 34 | (4aS,4bR,5S,6aS,6bR,9aS,10aS,10bS,12S)-4b,12-Difluoro-5-hydroxy-6b-(2-hydroxy-acetyl)-4a,6a-dimethyl-8-[4-(4-hydroxy-phenylsulfanylmethyl)-benzyl]-4a,4b,5,6,6a,6b,8,9,9a,10,10a,10b,11,12-tetradecahydro-7-oxa-8-aza-pentaleno[2,1-a]phenanthren-2-one |
| 37 | (4aS,4bR,5S,6aS,6bR,9aS,10aS,10bS,12S)-4b,12-Difluoro-5-hydroxy-6b-(2-hydroxy-acetyl)-4a,6a-dimethyl-8-[4-(4-hydroxy-phenylsulfanylmethyl)-phenyl]-4a,4b,5,6,6a,6b,8,9,9a,10,10a,10b,11,12-tetradecahydro-7-oxa-8-aza-pentaleno[2,1-a]phenanthren-2-one |
| 36 | (4aS,4bR,5S,6aS,6bR,9aS,10aS,10bS,12S)-4b,12-difluoro-5-hydroxy-4a,6a-dimethyl-8-[4-(4-hydroxy-phenylsulfanylmethyl)-benzyl]-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 35 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(5-methyl-2-thiophen-2-yl-oxazol-4-ylmethyl)-4a,4b,5,6,6a,6b,8,9,9a,10,10a,10b,11,12-tetradecahydro-7-oxa-8-aza-pentaleno[2,1-a]phenanthren-2-one |
| 50 | (4aS,4bR,5S,6aS,6bR,9aS,10aS,10bS,12S)-4b,12-difluoro-5-hydroxy-4a,6a-dimethyl-8-[4-(4-hydroxy-phenylsulfanylmethyl)-phenyl]-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester |
| 52 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-thiophen-2-yl-phenyl)4a,4b,5,6,6a,6b,8,9,9a,10,10a,10b,11,12-tetradecahydro-7-oxa-8-aza-pentaleno[2,1-a]phenanthren-2-one |
| 38 | (4aS,4bR,5S,6aS,6bR,9aS,10aS,10bS,12S)-8-Biphenyl-4-yl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 39 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-methoxyphenylsulfanylmethyl)-4a,4b,5,6,6a,6b,8,9,9a,10,10a,10b,11,12-tetradecahydro-7-oxa-8-aza-pentaleno[2,1-a]phenanthren-2-one |
| 40 | (4aS,4bR,5S,6aS,6bR,9aS,10aS,10bS,12S)-8-(4-Benzyl-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 41 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(4-pyridin-4-ylmethyl-phenyl)-4a,4b,5,6,6a,6b,8,9,9a,10,10a,10b,11,12-tetradecahydro-7-oxa-8-aza-pentaleno[2,1-a]phenanthren-2-one |
| 42 | (4aS,4bR,5S,6aS,6bR,9aS,10aS,10bS,12S)-4b,12-Difluoro-8-[4-(4-fluoro-benzylsulfanyl)-phenyl]-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 43 | (4aS,4bR,5S,6aS,6bR,9aS,10aS,10bS,12S)-8-[4-(4-Chloro-phenoxymethyl)-phenyl]-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 44 | (4aS,4bR,5S,6aS,6bR,9aS,10aS,10bS,12S)-4b,12-Difluoro-5-hydroxy-6b-(2-hydroxy-acetyl)-8-[4-(4-methoxy-phenoxymethyl)-phenyl]-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 45 | (4aS,4bR,5S,6aS,6bR,9aS,10aS,10bS,12S)-8-Biphenyl-3-yl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 46 | (4aS,4bR,5S,6aS,6bR,9aS,10aS,10bS,12S)-8-[4-(3-Chloro-phenoxymethyl)-phenyl]-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 47 | (4aS,4bR,5S,6aS,6bR,9aS,10aS,10bS,12S)-4b,12-Difluoro-5-hydroxy-6b-(2-hydroxy-acetyl)-4a,6a-dimethyl-8-(3-p-tolyloxymethyl-phenyl)-4a,4b,5,6,6a,6b,8,9,9a,10,10a,10b,11,12-tetradecahydro-7-oxa-8-aza-pentaleno[2,1-a]phenanthren-2-one |
| 48 | (4aS,4bR,5S,6aS,6bR,9aS,10aS,10bS,12S)-8-[4-(3-Chloro-benzylsulfanyl)-phenyl]-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one |
| 49 | (4aS,4bR,5S,6aS,6bR,9aS,10aS,10bS,12S)-4b,12-Difluoro-5-hydroxy-8-[4-(4-hydroxy-phenylsulfanylmethyl)-phenyl]-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid |

| Compound | Chemical Name |
|---|---|
| 51 | (4aS,4bR,5S,6aS,6bR,9aS,10aS,10bS,12S)-4b,12-Difluoro-5-hydroxy-8-[4-(4-hydroxy-phenylsulfanylmethyl)-benzyl]-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid | or pharmaceutically acceptable salts thereof.

According to procedures and methods analogous to those described in the present application, the following compounds of the invention may be obtained:

(4aS,4bR,5S,6aS,6bR,9aS,10aS,10bS,12S)-4b,12-difluoro-5-hydroxy-6b-(2-hydroxy-acetyl)-4a,6a-dimethyl-8-(4-p-tolylsulfanylmethyl-benzyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-4a,6a-dimethyl-2-oxo-8-(1-phenyl-1H-pyrrol-2-yl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(1-benzyl-1H-pyrrol-2-yl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-(5-phenyl-oxazol-2-yl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-(2-thiophen-2-yl-phenyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-(2-(5-Methyl-2-thiophen-2-yl-oxazol-4-ylmethyl))-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-(4-Benzyloxy-phenyl)-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-4a,6a-dimethyl-2-oxo-8-[4-(4-fluoro-benzyloxy)-phenyl]-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester; and pharmaceutically acceptable salts thereof.

The present invention also provides pharmaceutical compositions comprising a compound or salt thereof of the invention, and one or more pharmaceutically acceptable carriers and/or excipients.

The compounds and salts of the present invention may be administered as the sole active agent or in combination with other pharmaceutical active ingredients including those currently used in the treatment of respiratory disorders, e.g. beta2-agonists, antimuscarinic agents, corticosteroids, mitogen-activated protein kinases (P38 MAP kinase) inhibitors, nuclear factor kappa-B kinase subunit beta (IKK2) inhibitors, human neutrophil elastase (HNE) inhibitors, phosphodiesterase 4 (PDE4) inhibitors, leukotriene modulators, non-steroidal anti-inflammatory agents (NSAIDs), and mucus regulators.

The present invention also provides combinations of a compound or salt thereof of the present invention, with a β2-agonist selected from the group consisting of carmoterol, GSK-642444, indacaterol, milveterol, arformoterol, formoterol, salbutamol, levalbuterol, terbutaline, AZD-3199, BI-1744-CL, LAS-100977, bambuterol, isoproterenol, procaterol, clenbuterol, reproterol, fenoterol, and ASF-1020 and salts thereof.

The present invention also provides combinations of a compound or salt thereof of the present invention, with an antimuscarinic agent selected from the group consisting of aclidinium, tiotropium, ipratropium, trospium, glycopyrronium and oxitropium salts.

The present invention also provides combinations of a compound or salt thereof of the present invention, with a PDE4 inhibitor selected from the group consisting of AN-2728, AN-2898, CBS-3595, apremilast, ELB-353, KF-66490, K-34, LAS-37779, IBFB-211913, AWD-12-281, cipamfylline, cilomilast, roflumilast, BAY19-8004 and SCH-351591, AN-6415, indus-82010, TPI-PD3, ELB-353, CC-11050, GSK-256066, oglemilast, OX-914, tetomilast, MEM-1414, and RPL-554.

The present invention also provides combinations of a compound or salt thereof of the present invention, with a P38 MAP kinase inhibitor selected from the group consisting of semapimod, talmapimod, pirfenidone, PH-797804, GSK-725, minokine, and losmapimod and salts thereof.

In a preferred embodiment, the present invention provides combinations of a compound or a salt thereof of the present invention with an IKK2 inhibitor.

The present invention also provides combinations of a compound or a salt thereof of the present invention, with a FINE inhibitor selected from the group consisting of AAT, ADC-7828, Aeriva, TAPI, AE-3763, KRP-109, AX-9657, POL-6014, AER-002, AGTC-0106, respriva, AZD-9668, zemaira, AAT IV, PGX-100, elafin, SPHD-400, prolastin C, and prolastin inhaled.

The present invention also provides combinations of a compound or salt thereof of the present invention, with a leukotriene modulator selected from the group consisting of montelukast, zafirlukast, and pranlukast.

The present invention also provides combinations of a compound or salt thereof of the present invention, with a NSAID selected from the group consisting of ibuprofen and ketoprofen.

The present invention also provides combinations of a compound or salt thereof of the present invention, with a mucus regulator selected from the group consisting of INS-37217, diquafosol, sibenadet, CS-003, talnetant, DNK-333, MSI-1956, and gefitinib.

The present invention also provides a compound of the invention for use as a medicament.

The invention also relates to the use of compounds of the invention to decrease the number, activity, and movement of the inflammatory cells in vitro and/or in vivo.

The present invention is also directed to compounds of the invention for use in the prevention or treatment of any disease wherein the decrease in the number, activity, and movement of inflammatory cells is involved.

In a further aspect the present invention provides the use of compounds of the invention for the prevention and/or treatment of any disease wherein the decrease in the number, activity, and movement of inflammatory cells is involved.

In particular, compound of the inventions, either alone or combined with one or more active ingredients, may be administered for the prevention and/or treatment of a disease of the respiratory tract characterized by airway obstruction such as asthma and COPD.

In a further aspect, the present invention provides the use of compounds of the invention for the preparation of a medicament for the prevention and/or treatment of any disease wherein the decrease in the number, activity, and movement of inflammatory cells is involved.

Moreover the present invention provides a method for prevention and/or treatment of any disease wherein the decrease in the number, activity, and movement of inflammatory cells is involved, said method comprising administering to a patient in need of such treatment a therapeutically effective amount of a compound of the invention.

The present invention also provides pharmaceutical preparations of compounds of the invention suitable for administration by inhalation, by injection, orally or intra-nasally.

Inhalable preparations include inhalable powders, propellant-containing metering aerosols, or propellant-free inhalable formulations.

The present invention is also directed to a device which may be a single- or multi-dose dry powder inhaler, a metered dose inhaler or a nebulizer, in particular a soft mist nebulizer comprising a compound of the invention.

The present invention is also directed to a kit comprising the pharmaceutical compositions of compounds of the invention alone or in combination with or in admixture with one or more pharmaceutically acceptable carriers and/or excipients and a device which may be a single- or multi-dose dry powder inhaler, a metered dose inhaler, or a nebulizer.

The compounds of the present invention may be prepared according to a variety of synthetic steps which are carried out according to conventional methods and techniques or which are described below.

In one aspect, the present invention provides processes for the preparation of compounds of the invention and intermediates thereof.

In one embodiment, the present invention is directed to a process for the preparation of a compound of general formula (I'), wherein $R_1=(CH_2)_n-Z-(CH_2)_{n'}-R_4$, n=1, n'=0, Z, and $R_4$ are as defined above, which comprises (Route A, in Scheme 1):

the conversion of the hydroxyl group of 2-hydroxy acetyl moiety at position 6b of compounds of general formula (VI) into a leaving group (LG) of compounds of general formula (XI)

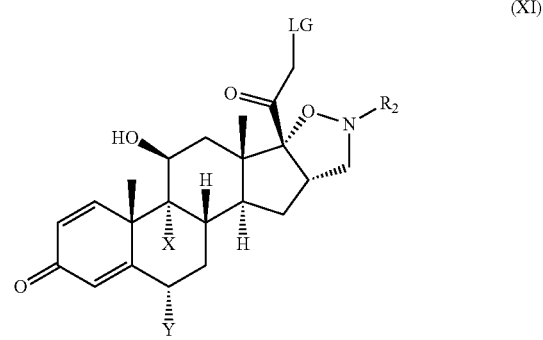

(XI)

wherein the LG may then be displaced by an appropriate nucleophile to give compounds of formula (I) as above defined.

The present invention is also directed to a process for the preparation of compounds of general formula (I'), wherein $R_1=(CH_2)_n-Z-(CH_2)_{n'}-R_4$, n and n'=0, Z, and $R_4$ are as defined above, which comprises (Route B1 in Scheme 1):

the reaction of a compound of formula (VI) to obtain a compound of general formula (XII)

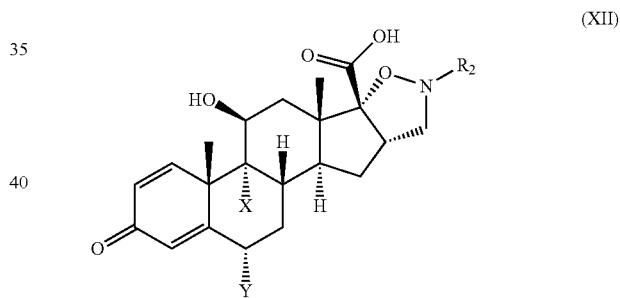

(XII)

the subsequent treatment of compound of formula (XII) with one or more equivalents of an acid activating agent and then with a nucleophile, to give compounds of formula (I) as above defined.

It will be then apparent to those skilled in the art that compounds of formula (I') wherein R1 is $-(CH_2)_n-Z-(CH_2)_{n'}-R_4$ and n=n'=0, Z=a bond, and $R_4$ is the group —OH, correspond to compounds of formula (XII) above reported and are thus also useful intermediates of synthesis for other compounds of the invention according to the synthetic routes herein described.

The present invention is also directed to a process for the preparation of compounds of general formula (I') wherein $R_1=(CH_2)_n-Z-(CH_2)_{n'}-R_4$ wherein n=n'=0, Z=S, and $R_4$ is as defined above, which comprises (Route B2 in Scheme 1):

the reaction of compounds of formula (VI) under oxidizing conditions to obtain the intermediates of general formula (XII)

its subsequent conversion into compounds of general formula (XIII)

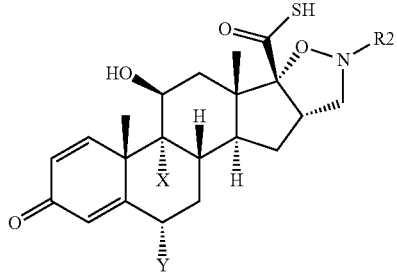
(XIII)

the subsequent alkylation of compound of formula (XIII): to give compounds of formula (I') as above defined.

The present invention is also directed to a process for the preparation of compounds of general formula (VI)

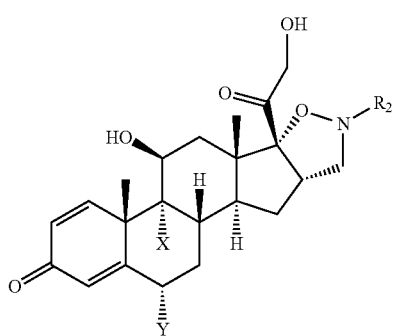
(VI)

which comprises (Route A1 in Scheme 1):
the reaction of a compound of general formula (IV)

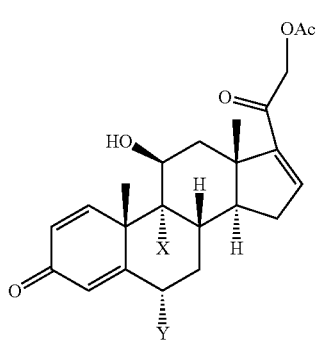
(IV)

with N-tetrahydropyranyl hydroxylamine (HO—NH—THP), to prepare a compound of formula (V)

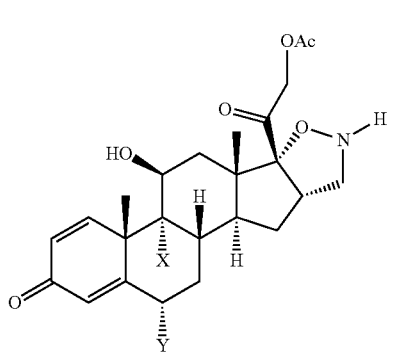
(V)

the further functionalization of compound of formula (V) by introduction of a group $R_2$ as above defined and
the subsequent removal of acetyl protection from hydroxy function; to give compounds of formula (VI) as above defined.

The present invention is also directed to a further process for the preparation of a compound of general formula (VI), which comprises (Route A2 in Scheme 1):
the reaction of a compound of formula (VII)

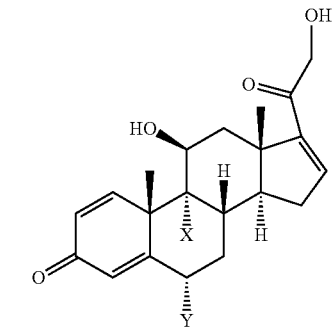
(VII)

with a compound of formula (X) and para formaldehyde

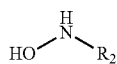
(X)

to give compounds of formula (VI) as above defined.

The present invention is also directed to another process for the preparation of a compound of general formula (VI), which comprises (Route A3 in Scheme 1):
the reaction of a compound of formula (VII) with N-tetrahydropyranyl hydroxylamine (HO—NH—THP) to obtain compound of formula (VIII)

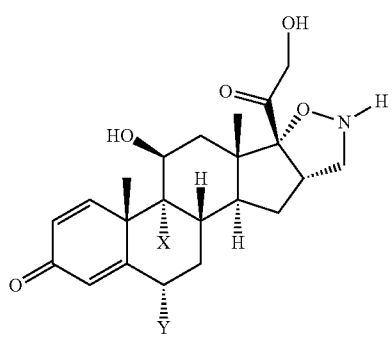
(VIII)

the subsequent protection of compound of formula (VIII) to obtain compound of formula (IX)

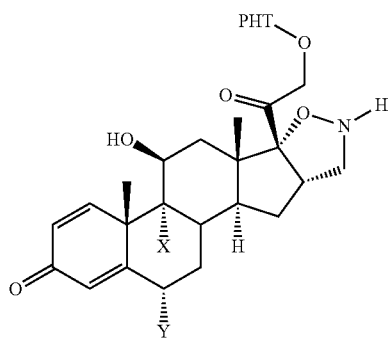
(IX)

the subsequent further functionalization of compound of formula (IX) and the final removal of protecting group from hydroxy function; to give compounds of formula (VI) as above defined.

The present invention is also directed to a process for the preparation of compounds of general formula (I'), wherein $R_1=(CH_2)_n-Z-(CH_2)_{n'}-R_4$, n and n'=0, Z=O, and $R_4$=Ac, which comprises the reaction of the intermediates of general formula (IV) with hydroxylamines of formula (X) and paraformaldehyde (Route C in Scheme 1).

The present invention is also directed to a process for the preparation of compounds of general formula (I'), wherein $R_1=(CH_2)_n-Z-(CH_2)_{n'}-R_4$, n=0, n'=1, $R_4$=F, and Z is a bond, which comprises (Route E in Scheme 1):

the reaction of compound (VII) with mesyl chloride and DIPEA in dry acetonitrile;

the subsequent in situ addition of tetra-n-butylammonium fluoride (TBAF) and KI and the subsequent cycloaddition reaction of the obtained intermediate (XV) with HO—NH—THP and paraformaldehyde

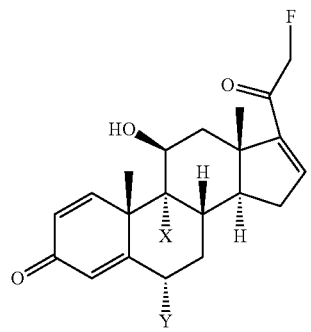

(XV)

the subsequent nitrogen functionalization to give compounds of formula (I) as above defined.

In preferred embodiment of the invention, all the processes herein described are performed with compounds and intermediates where X and Y are fluorine.

From all of the above, it is clear to the person skilled in the art that by selecting the starting material with a proper stereochemical configuration, any of the possible stereoisomers of formula (I) could be thus obtained.

Some of the processes which can be used for the preparation of the compounds of formula (I'), as described in Scheme 1A and Scheme 1B, may also be applied to compounds of formula (I).

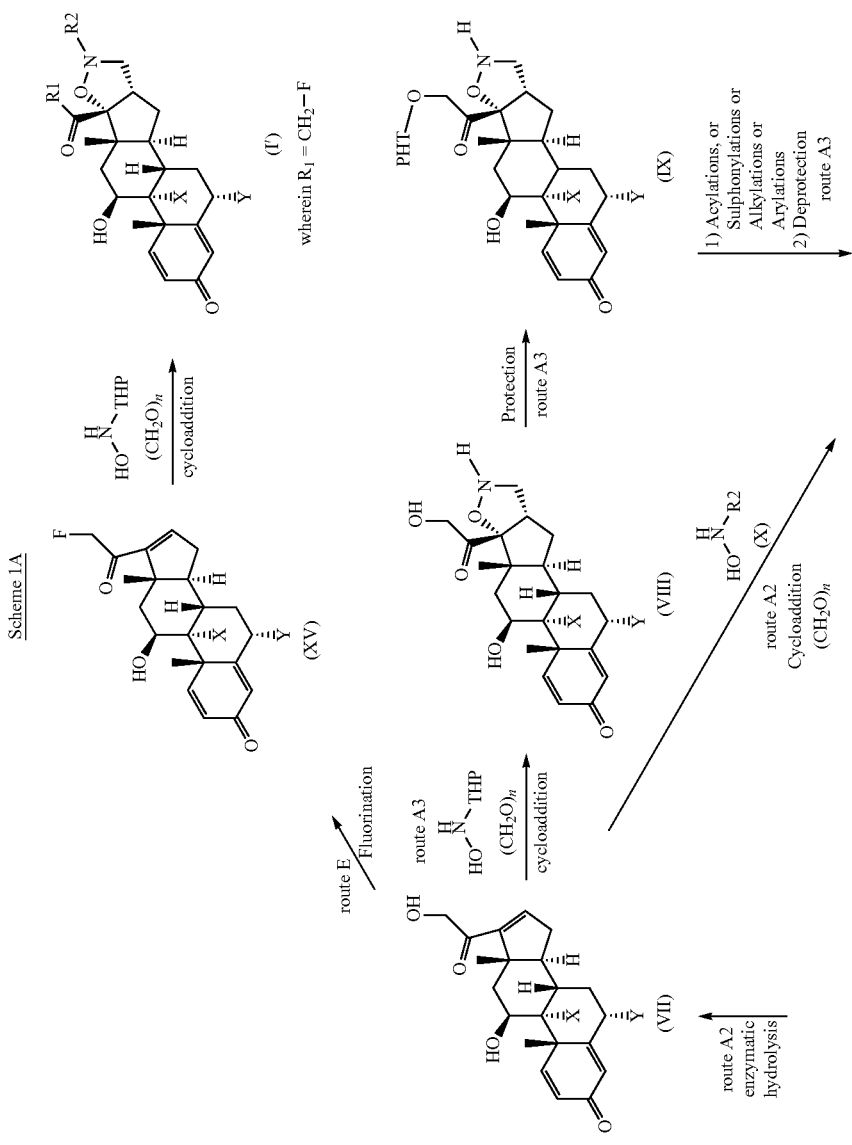

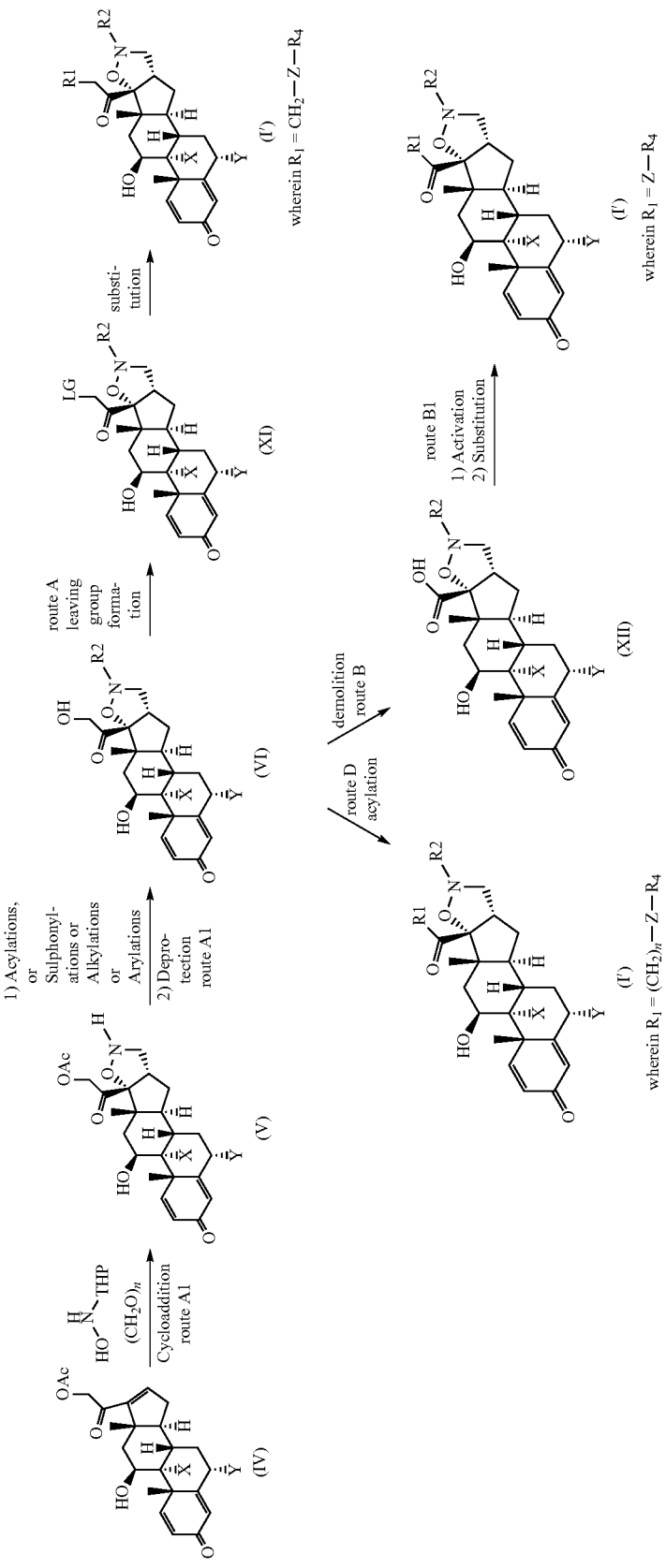

Scheme 1B
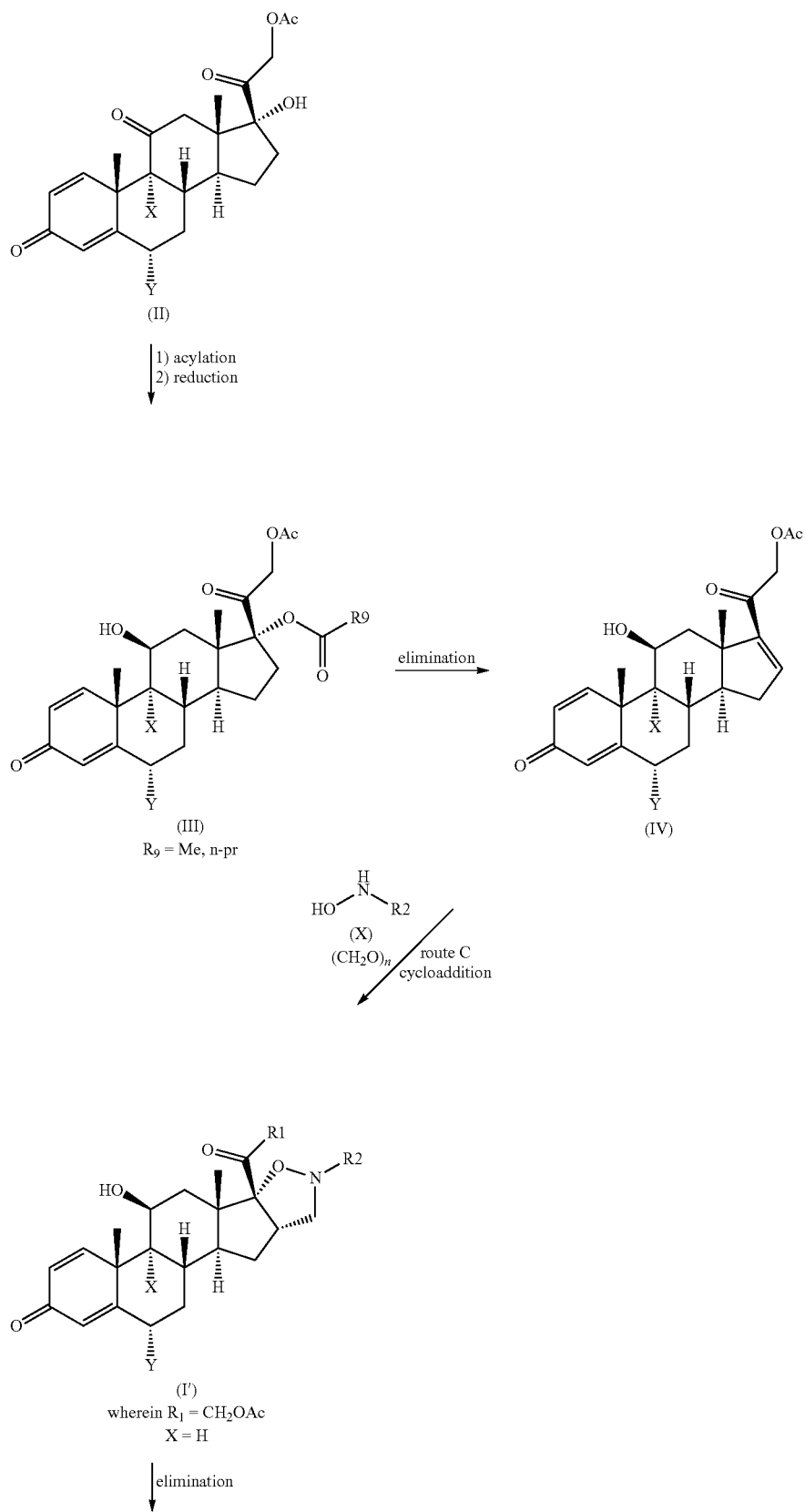

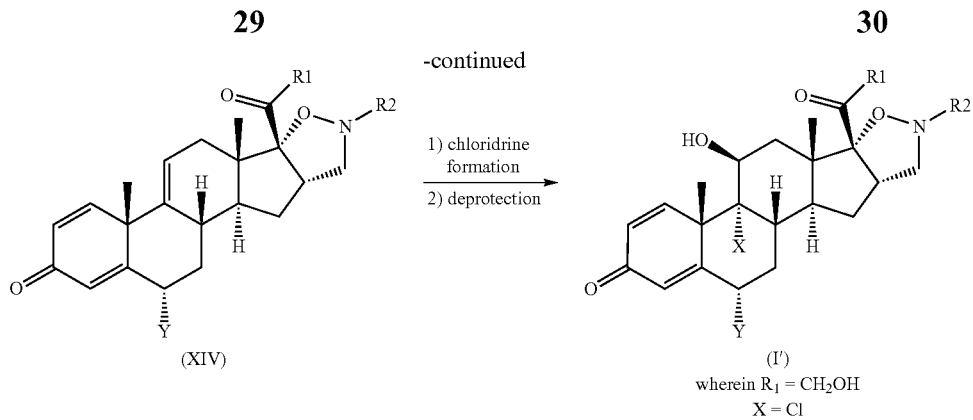

1) chloridrine formation
2) deprotection (XIV)

(I')
wherein R₁ = CH₂OH
X = Cl

Procedure for the Preparation of the Compounds of the Invention

According to particular embodiments, the compounds of the invention may be prepared according to different routes described in scheme 1, depending on the nature of the substituents $R_1$ and $R_2$.

Route A1—the reaction of compounds of general formula (IV) with N-tetrahydropyranyl hydroxylamine (HO—NH—THP), to prepare a compound of formula (V), can be conveniently conducted in a protic solvent such as EtOH at a temperature ranging from 80 to 100° C. The THP protecting group is directly cleaved in the reaction conditions.

These compounds may be further functionalized with alkyl halides, acyl halides, isocyanates, carbamoyl chlorides, or sulphonyl chlorides using method readily apparent for those skilled in the art (see *J. Med. Chem.*, 379-388, 1995; *J. C. S. Chem. Comm.*, 256-257, 1985, both of which are incorporated herein by reference in their entireties), to give compounds of general formula (VI). These reactions are usually carried out in a solvent such as dichloromethane (DCM) or tetrahydrofuran (THF) and proceed at a temperature range from room temperature (RT) to reflux. A base such as triethylamine or diisopropylethylamine may be required to promote the reaction. The reaction with aryl halides may be performed under the known copper catalyzed N-arylation of isoxazolidine (see *Bioorg. Med. Chem. Lett.*, 2834, 2005, which is incorporated herein by reference in its entirety). The acetyl ester may be easily hydrolyzed using standard conditions for the deacetylation of alcohols, treating for example the compound with a base such as sodium or potassium hydroxide or potassium carbonate in a suitable solvent (e.g. methanol or ethanol). This reaction usually proceeds at RT over a period of 1 to 5 hours leading to compounds of general formula (VI).

Compounds of general formula (IV) may be conveniently prepared according to standard procedures reported in the literature. For instance they may be prepared by treatment of compounds of general formula (III) with a base such as potassium acetate. This reaction is usually performed in a suitable polar solvent such as dimethylformamide (DMF) and typically proceeds at a temperature range from 80 to 110° C., over a period of 0.5 to 4 hours.

Compounds of formula (III) may be readily prepared from known compounds by well known methods, starting from compounds of general formula (II) (see *J. Med. Chem.*, 1982, 25, 1492-1495, which is incorporated herein by reference in its entirety).

Route A2—alternatively, the compounds of general formula (VI) may be prepared starting from the reaction of a compound of formula (VII) with a compound of formula (X) in the presence of paraformaldehyde, using known procedures for the isoxazolidine formation, by cycloaddition of nitrones (see *J. Med. Chem.*, 25, 1492-1495, 1982, which is incorporated herein by reference in its entirety). The reaction is conveniently carried out in a protogenic solvent, such as ethanol, at temperatures ranging from 80 to 100° C. Hydroxyl amine of formula (X) are either commercially available or may be easily prepared using procedures well known for those skilled in the art, for example by reducing an oxime with a reducing agent, such as borane pyridine complex (see *J. Med. Chem.*, 40, 1955-1968, 1997, which is incorporated herein by reference in its entirety) or by reaction of O-tetrahydropyranyl hydroxylamine with a suitable alkylating agent such as alkyl halides (see *Chem. Pharm. Bull.*, 46, 966-972, 1998, which is incorporated herein by reference in its entirety).

The compounds of formula (VII) may be prepared hydrolyzing the compounds of formula (IV). This reaction is preferably carried out by subjecting compounds (IV) to the action of an enzyme, such as immobilized Lipase from *Candida antarctica* (Sigma Aldrich) (see *Tetrahedron*, 50, 13165-13172, 1994, which is incorporated herein by reference in its entirety).

Route A3—compounds of general formula (VIII) may be prepared starting from the reaction of a compound of formula (VII) with HO—NH—THP. This reaction may be conveniently conducted in dioxane or in a protic solvent such as EtOH at a temperature ranging from 80 to 100° C. The THP protecting group is directly cleaved in the reaction conditions. The obtained (VIII) can be conveniently and selectively protected by treatment with dihydropyran in a suitable solvent such as DCM or THF, at temperature from 0° C. to RT, to obtain compound of formula (IX). The reaction is complete in time ranging from 0.5 to 3 hours. Compounds of formula (IX) may be further functionalized with alkyl halides, acyl halides, isocyanates, carbamoyl chlorides or sulphonyl chlorides as described in Route A1. The THP protecting group can be easily removed by treating the protected intermediate with HCl in a suitable solvent, such as THF or dioxane. This reaction usually proceeds at RT over a period of 1 to 15 hours leading to compounds of general formula (VI).

Route A—conversion of the hydroxyl group of 2-hydroxy acetyl moiety at position 6b of compounds of general formula (VI) into a leaving group (LG) of compounds of general formula (XI) can be carried out by treating compounds of formula (VI) with methanesulfonyl chloride or p-toluenesulphonyl chloride (see March's, "Advanced Organic Chemistry", Wiley-Interscience, which is incorporated herein by reference in its entirety), in a suitable solvent, such as pyridine. This reaction is usually performed at RT over a period of 1 to 5 hours.

The LG of compounds of general formula (XI) may be easily displaced by nucleophiles such as halide anions, alcohols, thiols, thioacids, amines, amides and carbanions (see *J. Org. Chem.*, 1042, 1999; *J. Steroid. Biochem.*, 13, 311-322, 1980, both of which are incorporated herein by reference in their entireties), to obtain compounds of general formula (I) and (I') wherein $R_1=(CH_2)_n-Z-(CH_2)_{n'}-R_3$, n=1, n'=0, Z is a bond, and $R_4$ is as defined above. The reaction is usually performed in a suitable solvent, such as DCM, THF or DMF, in a range of temperature from 0 to 80° C. over a period of 1-5 hours and may be promoted by a base such as sodium or potassium carbonate or sodium hydride. The obtained product may be further functionalized modifying the moiety introduced by the described nucleophilic substitution reaction.

Route B—reaction of compounds of formula (VI) under well known oxidation conditions to obtain the intermediates of general formula (XII). This reaction is usually performed in open air at RT over a period of 12 to 48 hours, in a suitable solvent such as THF in the presence of aqueous solution of an inorganic base, such as sodium or potassium hydroxide.

Route B1—conversion of the intermediates of formula (XII) into compounds of general formula (I) and (I') wherein $R_1=(CH_2)_n-Z-(CH_2)_{n'}-R_4$, n and n'=0, Z, and $R_4$ are as defined above, by treating the acid (XII) with one or more equivalents of an acid activating agent such as carbonyldiimidazole. The reaction is usually performed in a suitable polar solvent such as DMF, in a range of temperature from 0 to 80° C. over a period of 1-2 hours. The activated acid may be reacted with a nucleophile, such as alcohols, thiols, thioacids and amines. The reaction may be promoted by a base such as sodium or potassium carbonate, sodium hydride and proceeds at a temperature ranging from 0 to 20° C. over a period of 1 to 24 hours.

Alternatively, the intermediates of formula (XII) may be converted into the corresponding acyl chloride under well known conditions, using oxalyl chloride in a suitable solvent such as DCM. The activated intermediate may be reacted with a nucleophile such as alcohols, thiols, thioacids, amines, and carbanions such as alkyl, aryl and heteroaryl cuprates or other metallorganic compounds reported in the literature, to be suitable for the conversion of acyl chlorides into the corresponding ketones.

Route B2—conversion of intermediates of formula (XII) into compounds of general formula (XIII), derived from reaction of acid (XII) with carbonyldiimidazole, followed by reaction with the sodium salt of thioacetic acid and/or anhydrous hydrogen sulphide. The reaction is usually performed adding the solution of the preformed salt in the reaction solvent to the solution of the activated acid at a temperature ranging from 0 to 20° C. The thioacid intermediate (XIII) readily formed is in situ reacted with an alkylating reagent, such as bromoalkanes, leading to thioesters of general formula (I) and (I') wherein $R_1=(CH_2)_n-Z-(CH_2)_{n'}-R_4$, n and n'=0, Z=S, and $R_4$ is as defined above. The choice of suitable bromoalkane, such as bromo-chloromethane, may allow the preparation of compounds of formula (I) and (I') wherein $R_1=(CH_2)_n-Z-(CH_2)_{n'}-R_3$, n and n'=0, Z=S, and $R_4$ is as defined above, that may be further modified. For example, the reaction of these compounds in which $R_4$ is chloromethyl with potassium iodide, followed by treatment with silver fluoride, may allow the preparation of compounds of formula (I) and (I') in which $R_3$=fluoromethyl. These reactions are well known to those skilled in the art (see *J. Med. Chem.*, 37, 3717-3729, 1994, which is incorporated herein by reference in its entirety).

Route C—reaction of the intermediates of general formula (IV) with hydroxylamines of formula (X) in the presence of paraformaldehyde using known procedures for the isoxazolidine formation by cycloaddition of nitrones. The reaction is conveniently performed in a protogenic solvent, such as ethanol. The reaction is conveniently carried out at high temperature, for example from 60 to 85° C. and leads to compounds of general formula (I) and (I') wherein $R_1=(CH_2)_n-Z-R_4$, wherein n=1, Z=O, and $R_4$=Ac.

The intermediates of general formula (XIV) may be prepared by treating compounds of general formula (I) and (I') wherein $R_1=(CH_2)_n-Z-R_4$, wherein n=1, Z=O, $R_4$=Ac and X=H, with methanesulfonyl chloride in a suitable solvent, such as DMF, in the presence of a base, such as pyridine. The reaction proceeds at a temperature ranging from 80 to 100° C. over a period of 1 to 5 hours.

By reacting compounds of formula (XIV) under well known conditions for the preparation of chlorohydrine starting from the corresponding alkene, it is possible to obtain compounds of general formula (I) and (I') wherein $R_1=(CH_2)_n-Z-R_4$, wherein n=1, Z=O, $R_4$=H and X=Cl. The reaction involves the use of a chlorinating agent, such as N-chlorosuccinimide or dichloro-5,5-dimethylhydantoin, and is promoted by an acid such as perchloric acid. The reaction is usually carried out in a polar solvent such as THF, in a range of temperature from 0 to 20° C. over a period of 1 to 4 hours. The acetyl ester of compounds of formula (XIV) may be easily hydrolyzed using standard conditions for the deacetylation of alcohols, treating for example the compound with a base such as sodium or potassium carbonate in a solvent such as methanol or ethanol. This reaction usually proceeds at low temperature, ranging from 0 to 20° C., over a period of 0.5 to 2 hours.

Route D—reaction of the intermediates of general formula (VI) with acyl chlorides, using procedures well known for those skilled in the art. The reaction is conveniently performed in DCM as solvent in the presence of a base such as triethylamine, at room temperatures over a period of 20 to 50 hours. This procedure may allow the preparation of compounds of formula (I') wherein $R_1=(CH_2)_n-Z-(CH_2)_{n'}-R_4$, n=1, n'=0, Z=O, $R_3$ are as defined above.

Route E—reaction of compound (VII) with mesyl chloride and N,N-diisopropylethylamine (DIPEA) in dry acetonitrile. Then, the introduction of fluorine atom can be conveniently performed by in situ addition of tetra-n-butylammonium fluoride (TBAF) and KI and heating over a period of 8 to 20 hours. Cycloaddition reaction of the obtained intermediate (XV) with hydroxylamines of formula (X) in the presence of paraformaldehyde, under the known conditions described in Route C, lead to the formation of compounds of general formula (I'), wherein $R_1=(CH_2)_n-Z-(CH_2)_{n'}-R_4$, n=0, n'=1, Z is a bond, $R_4$=F, and $R_2$ as defined above.

Hydroxylamines of formula (X) are either commercially available or may be prepared according to different synthetic routes, some of which are well known.

In one aspect of the present invention, synthetic routes for the preparation of hydroxylamines of formula (X) are provided as described in Scheme 2.

Scheme 2

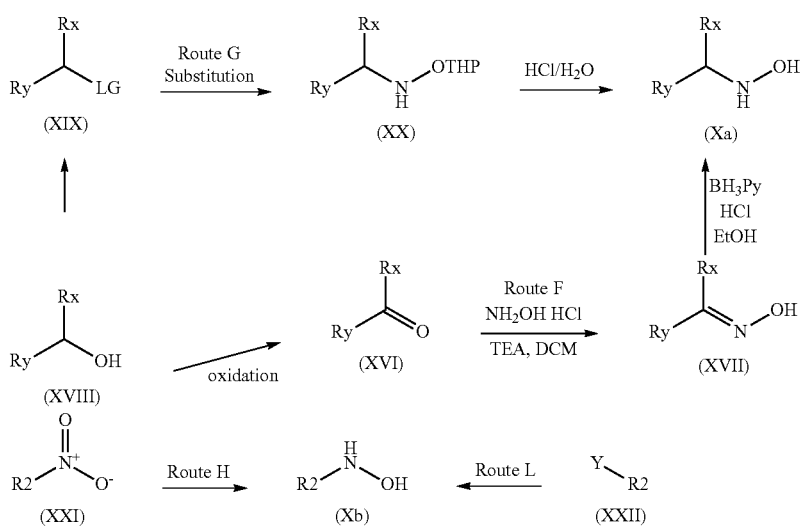

Route F—reaction of compounds of general formula (XVI) with hydroxylamine hydrochloride (NH₂OH HCl) in presence of triethyl amine, to prepare an oxime of formula (XVII) can be conveniently conducted in DCM as solvent at a temperature ranging from RT to 50° C.

These compounds [oximes of general formula (XVII)] may be reduced to hydroxylamines of general formula (Xa), wherein $R_x$ and $R_y$ may assume different meanings within the scope of the instant invention, with a reducing agent such as, for example, borane pyridine complex and HCl in polar protic solvents such as ethanol at RT (see *Tetrahedron* 1992, Vol. 47, No. 17, 3557-3570; J. Med. Chem. 1997, 40, 1955-1968, both of which are incorporated herein by reference in their entireties). Compounds of general formula (XVI) are commercially available or can be obtained by oxidation of compounds of general formula (XVIII) by well known procedures (for example Swern oxidation: see *J.A.C.S.*, 2005, 127, 29, 10396, which is incorporated herein by reference in its entirety).

Route G—Alternatively, the compounds of general formula (Xa) may be prepared by the reaction of an activated compound of general formula (XIX), where LG is a suitable leaving group, such as for example an halide (Cl, Br or I), a mesylate, a tosylate or another leaving group, with O-tetrahydropyranyl hydroxylamine (NH₂OTHP) to generate an intermediate of formula (XX), using well known procedures (see *J.A.C.S.*, 2000, 122, 18, 4522; Tetrahedron 1999, 55, 41, 12069, both of which are incorporated herein by reference in their entireties), and subsequent deprotection of the THP protective group. The substitution reaction is conveniently carried out in DMF, ethanol or acetonitrile as solvents, in the presence of different kind of bases such as $K_2CO_3$ or DIPEA and at temperatures ranging from RT to 80° C. Compounds of general formula (XIX) may be commercially available or may be prepared starting from an alcohol of general formula (XVIII) and converting the hydroxyl group into the suitable leaving group by known procedures. For example, mesylates can be conveniently obtained from alcohols (XVIII) with mesylchloride and TEA in DCM (see *Organic Letters*, 2002, vol. 4, No. 15, 2485, which is incorporated herein by reference in its entirety).

Route H—Hydroxylamines of general formula (Xb), wherein R2 is optionally substituted aryl or heteroaryl, may be prepared starting from the corresponding nitro-aryl or nitro-heteroaryl compounds. For example, nitro compounds (XXI) can be conveniently reduced to hydroxylamines (see *Synthetic Communications*, 1997, Vol. 27, No. 20, 3497-3504, which is incorporated herein by reference in its entirety) with $BiCl_3$ and $KBH_4$ in polar protic solvents, such as ethanol at RT. Alternatively, aryl or heteroaryl hydroxylamines (Xb) may be conveniently obtained by reduction of nitro compounds (XXI) with hydrazine in the presence of Raney nickel in an appropriate mixture of solvents, such as ethanol and dichloromethane (see *Synthesis*, 1984, 11, 938-941, which is incorporated herein by reference in its entirety) or with hydrazine hydrate in the presence of rhodium on carbon in tetrahydrofuran as solvent (see *J. Med. Chem.*, 1987, 30, 2, 400; *Eur. J. Org. Chem.*, 2006, 16,3707, both of which are incorporated herein by reference in their entireties). It is necessary, in this procedure, to control the temperature between 0 and 10° C. Finally, another convenient reductive method to afford compounds of general formula (Xb), entails the reduction of compounds (XXI) with Zn and $NH_4Cl$ (see *Tetrahedron Letters*, 2005, Vol. 46, No. 35, 5913-5918; *J. Org. Chem.*, 1982, 47, 7, 1171 both of which are incorporated herein by reference in their entireties), in different polar solvents such as acetone or ethanol.

Route L—Alternatively, aryl or heteroaryl hydroxylamines of general formula (Xb) as above defined, may be prepared by nucleophilic aromatic substitution from aryl or heteroaryl electron-poor chlorides or fluorides with hydroxylamine, using methods readily apparent for those skilled in the art. For example, reaction of a compound of general formula (XXII), wherein Y is a suitable leaving group such as chlorine or fluorine, with aqueous hydroxylamine in ethanol (see *J. Med. Chem.*, 2009, 52, 19, 5974, which is incorporated herein by reference in its entirety) may give hydroxylamines of general formula (Xb). The reaction is conducted at reflux in time ranging from 6 to 10 hours. Different methods (see WO 2006/74187, which is incorporated herein by reference in its entirety) entail reaction of the suitable aryl or heteroaryl electron-poor chlorides or fluorides with hydroxylamine hydrochloride in polar protic solvents, such as isopropanol. The reaction can be conveniently conducted under microwave heating at a temperature of 130° C., in time ranging from 15 to 25 hours.

Advantageously, the compounds of the present invention may be administered for example, at a dosage comprised between 0.001 and 1000 mg/day, preferably between 0.1 and 500 mg/day.

When they are administered by inhalation route, the dosage of the compounds of compounds of the invention is advantageously comprised between 0.01 and 20 mg/day, preferably between 0.1 and 10 mg/day.

Of course, the exact dosage will depend on the identity of the compound or salt being administered, the route of administration, the condition being treated, and the age, weight, and condition of the patient, and may be easily determined by a doctor treating the patient.

Preferably, the compounds of the present invention alone or combined with other active ingredients may be administered for the prevention and/or treatment of any obstructive respiratory disease such as asthma, chronic bronchitis and chronic obstructive pulmonary disease (COPD).

However the compounds of the present invention may be administered for the prevention and/or treatment of any disease wherein the decrease in the number, activity and movement of inflammatory cells is involved.

Examples of such diseases include: diseases involving inflammation such as asthma and other allergic disorders, COPD, acute rhinitis; reverse acute transplant rejection and acute exacerbations of selected autoimmune disorders, graft-versus-host disease in bone-marrow transplantation; autoimmune disorders such as rheumatoid and other arthritis; skin conditions such as systemic lupus erythematosus, systemic dermatomyositis, psoriasis; inflammatory bowel disease, inflammatory ophthalmic diseases, autoimmune hematologic disorders, and acute exacerbations of multiple sclerosis; kidney, liver, heart, and other organ transplantation; Behçet's acute ocular syndrome, endogenous uveitis, atopic dermatitis, inflammatory bowel disease, and nephrotic syndrome; Hodgkin's disease and non-Hodgkin's lymphoma, multiple myeloma and chronic lymphocytic leukemia (CLL); autoimmune hemolytic anemia and thrombocytopenia associated with CLL; leukemia and malignant lymphoma. Preferably the compounds of the invention may be administered for the prevention and/or treatment of respiratory diseases such as from mild to acute severe conditions of asthma and COPD.

Other features of the invention will become apparent in the course of the following descriptions of exemplary embodiments which are given for illustration of the invention and are not intended to be limiting thereof.

EXAMPLES

In the reported experimental procedures, the following abbreviations may be used: TEA=triethylamine; DCM=dichloromethane; RT=room temperature; AcOEt=ethyl acetate; DMF=N,N-dimethylformamide; DMSO=dimethylsulfoxide; HATU=O-(7-Azabenzotriazol-1-yl)-N,N,N,N-tetramethyluronium hexafluorophosphate; MeOH=methyl alcohol.

$^1$H NMR spectra were recorded with a Bruker Avance II 300 Spectrometer Probehead 5 mm BBI 1H-BB (inverse probe head). Chemical shifts are reported in ppm downfield from TMS as internal standard.

Mass spectra were recorded with Waters micromass ZQ, with mass conditions: ESI POS 3.2 KV, Cone Voltage 25V, 350° C.

Liquid chromatography has been performed with Waters HPLC Acquity equipped with column Acquity UPLC BEH C18 1.7 μm 2.1×50 mm and detector UV: Waters Acquity 2996 PDA. Elution was made with two solvent systems: solvent A (H$_2$O-ACN 95:5+0.1% TFA) and solvent B (H$_2$O-ACN 5:95+0.1% TFA), from initial 95% of solvent A to 100% of solvent B over 7 minutes.

Optical rotations were measured using the sodium-D line, with a Perkin Elmer polarimeter Mod 341.

Example 1

Preparation of 4-(4-fluoro-benzyloxy)-benzaldehyde oxime (Intermediate 1)

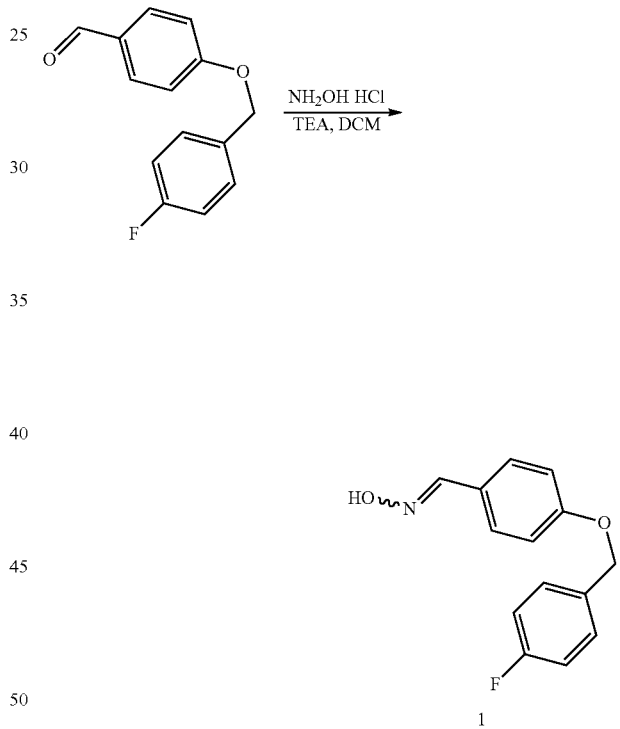

To a mixture of 4-(4-fluoro-benzyloxy)-benzaldehyde and hydroxylamine hydrochloride (0.664 g, 9.56 mmol) in anhydrous DCM (30 ml), at 0° C. under nitrogen atmosphere, TEA (1.332 ml, 9.56 mmol) was added dropwise, and the reaction mixture was stirred at RT overnight. The mixture was directly purified by flash chromatography on silica gel, in gradient elution from petroleum ether/AcOEt 85:15 to ether/AcOEt 70:30 to afford the title compound 1 (2.03 g, 8.28 mmol, 95% yield).

LC-MS (ESI POS): 246.0 (MH+)

With an analogous procedure to that described in Example 1 and starting from appropriate aldehydes as starting materials, the intermediates in Table 1 hereinbelow reported were prepared.

TABLE 1

| Intermediate | Structure | Analytical |
|---|---|---|
| 10 | 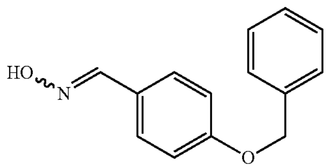 [SMILES: ON=Cc1ccc(OCc2ccccc2)cc1] | LC-MS (ESI POS): 228.0 MH+ |
| 15 | 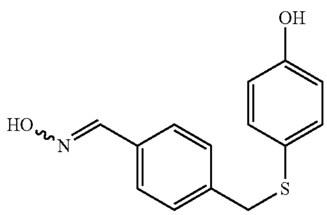 [SMILES: ON=Cc1ccc(CSc2ccc(O)cc2)cc1] | LC-MS (ESI POS): 260.0 MH+ |
| 16 | 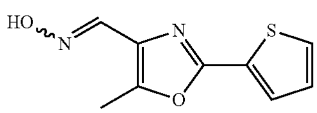 | LC-MS (ESI POS): 208.9 MH+ |

Example 2

Preparation of
N-[4-(4-fluoro-benzyloxy)-benzyl]-hydroxylamine
(Intermediate 2)

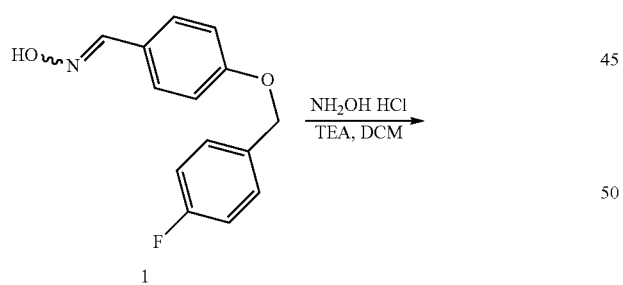

2.86 M (10%) aqueous HCl (17.64 ml, 50.4 mmol) was added dropwise to a stirred solution of 1 (1.237 g, 5.04 mmol) and boranepyridine complex (2.081 ml, 16.64 mmol) in absolute ethanol (25 ml) at 0° C., under nitrogen atmosphere. After the addition was complete, the mixture was stirred at 0° C. for 10 minutes and at RT for 1 hour, basified to pH 9 with solid sodium bicarbonate and sodium carbonate, and extracted with DCM (3×100 ml). The combined organic layers were dried ($Na_2SO_4$) and evaporated in vacuo, to afford the desired compound 2 (1.17 g, 4.73 mmol, 94% yield) as an off-white solid, which was used without further purification.

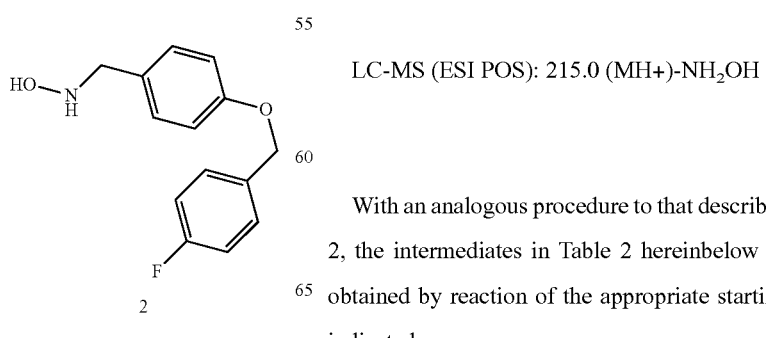

LC-MS (ESI POS): 215.0 (MH+)-$NH_2OH$

With an analogous procedure to that described in Example 2, the intermediates in Table 2 hereinbelow reported were obtained by reaction of the appropriate starting material as indicated.

TABLE 2

| Intermediate | Structure | Starting Material Ref | Analytical |
|---|---|---|---|
| 11 | 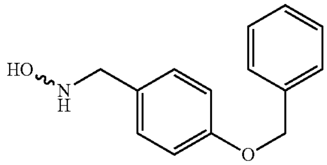 [SMILES: ONCc1ccc(OCc2ccccc2)cc1] | Int. 10 | LC-MS (ESI POS): 197.0 (MH+)—NH$_2$OH |
| 17 | 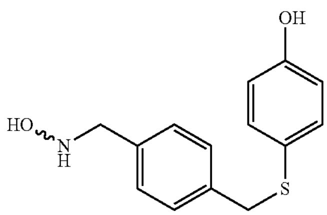 [SMILES: ONCc1ccc(CSc2ccc(O)cc2)cc1] | Int. 15 | LC-MS (ESI POS): 229.0 (MH+)—NH$_2$OH |
| 18 | 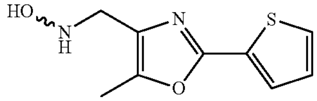 | Int. 16 | LC-MS (ESI POS): 210.8 (MH+) |

Example 3

Preparation of acetic acid 2-((6S,9R,10S,11S,13S)-6,9-difluoro-11-hydroxy-10,13-dimethyl-3-oxo-6,7,8,9,10,11,12,13,14,15-decahydro-3H-cyclopenta[a]phenanthren-17-yl)-2-oxo-ethyl ester (Intermediate 4)

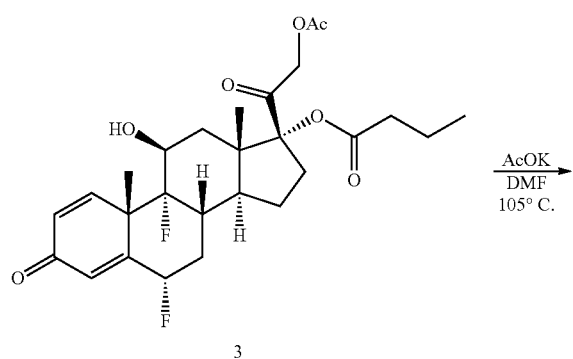

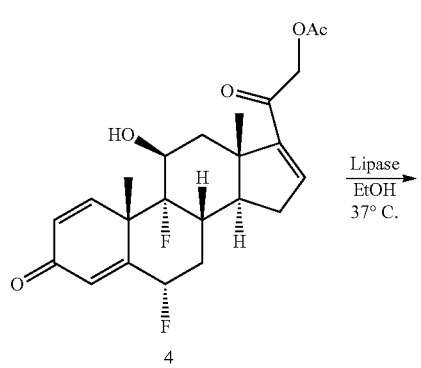

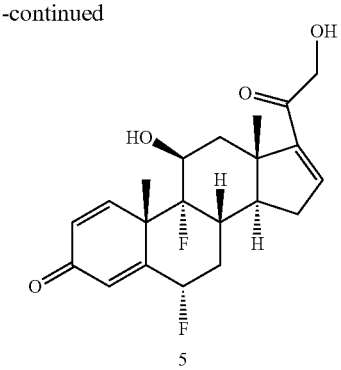

To a solution of butyric acid (9R,10S,11S,13S,17R)-17-(2-acetoxy-acetyl)-9-chloro-11-hydroxy-10,13-dimethyl-3-oxo-6,7,8,9,10,11,12,13,14,15,16,17-dodecahydro-3H-cyclopenta[a]phenanthren-17-yl ester (intermediate 3) (2.48 g, 4.88 mmol) in anhydrous DMF (60 ml), under nitrogen atmosphere, potassium acetate (3.83 g, 39.0 mmol) is added, and the reaction mixture is stirred at 100° C. for 1.5 hours. The cooled reaction mixture is poured into ice and brine (200 ml), and the aqueous layer is extracted with AcOEt (3×150 ml). The combined organic extracts are washed with water and brine, dried over Na$_2$SO$_4$, and concentrated to afford 2.55 g of crude title compound 4 which is used in the next step without further purification.

$^1$H NMR (300 MHz, DMSO-d$_6$): ppm 7.29 (dd, 1 H), 6.99 (dd, 1 H), 6.29 (dd, 1H), 5.98-6.15 (m, 1 H), 5.68 (dddd, 1 H), 5.56 (dd, 1 H), 5.10 (d, 1 H), 4.92 (d, 1 H), 3.98-4.23 (m, 1 H), 2.56-2.83 (m, 1 H), 2.26-2.44 (m, 3 H), 2.14-2.26 (m, 1 H), 2.09 (s, 3 H), 1.71-1.87 (m, 1 H), 1.55-1.65 (m, 2 H), 1.53 (s, 3 H), 1.15 (s, 3 H).

LC-MS (ESI POS): 421.97 (MH+)

Preparation of (6S,9R,10S,11S,13S)-6,9-difluoro-11-hydroxy-17-(2-hydroxy-acetyl)-10,13-dimethyl-6,7,8,9,10,11,12,13,14,15-decahydro-cyclopenta[a]phenanthren-3-one (Intermediate 5)

To a solution of (intermediate 4) (2.55 g, 6.06 mmol) in ethanol (100 ml), *Candida Antarctica* Lipase (2 U/mg) (510 mg, 6.06 mmol) is added, and the reaction mixture is stirred at 37° C. overnight. The reaction mixture is filtered and washed with methanol, and the residue is purified by flash chromatography on silica gel, in gradient elution from DCM/AcOEt 90:10 to DCM/AcOEt 50:50, to afford 1.62 g of title compound 5 (70.6% yield).

$^1$H NMR (300 MHz, DMSO-$d_6$): ppm 7.29 (dd, 1 H), 6.87 (dd, 1 H), 6.29 (dd, 1H), 6.09-6.17 (m, 1 H), 5.67 (dddd, 1 H), 5.53 (dd, 1 H), 4.77 (t, 1 H), 4.44 (dd, 1 H), 4.26 (dd, 1 H), 4.04-4.15 (m, 1 H), 2.56-2.79 (m, 1 H), 2.39 (dd, 1 H), 2.25-2.35 (m, 2H), 2.09-2.25 (m, 1 H), 1.76 (td, 1 H), 1.55-1.66 (m, 2 H), 1.53 (s, 3 H), 1.17 (s, 3 H).

LC-MS (ESI POS): 379.99 (MH+)

Example 4

Preparation of 4-(4-(hydroxyamino)benzylthio)phenol (Intermediate 19)

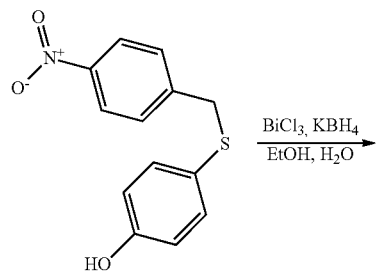

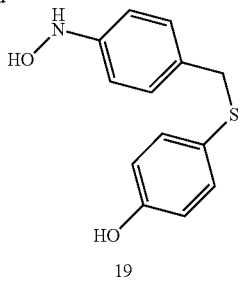

A suspension of 4-(4-nitro-benzylsulfanyl)-phenol (647 mg, 2.476 mmol) and bismuth(iii) chloride (156 mg, 0.495 mmol) in EtOH (30 ml) and water (10 ml) was cooled to 0° C., under nitrogen atmosphere. Then potassiumborohydride (134 mg, 2.476 mmol) was added in small portions. The suspension turned into black, and it was stirred at 0° C. for 2 hours. Further potassiumborohydride (40.1 mg, 0.743 mmol) was added, and the mixture was stirred at 0° C. for 1 hour. Diethyl ether was added, and the mixture was treated with HCl 0.5 N until pH=7 with continuous bubbling of nitrogen.

The mixture was partitioned between water and diethyl ether, and the organic phase was dried over $Na_2SO_4$ and filtered. The solvent was evaporated to give Intermediate 19 (597 mg, 2.414 mmol, 97% yield) as a pale yellow solid. The crude was used as such in the following step.

LC-MS (ESI POS): 231.0 (MH+)-OH

With an analogous procedure to that described in Example 4, the intermediates in Table 3 herein below were obtained starting from appropriate starting material.

TABLE 3

| Intermediate | Structure | Analytical |
|---|---|---|
| 20 | 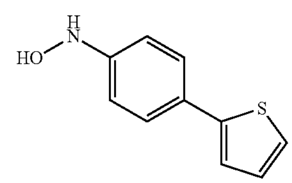 [SMILES: ONc1ccc(-c2cccs2)cc1] | LC-MS (ESI POS): 175.0 (MH+)—OH |
| 21 | 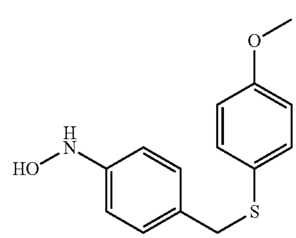 | LC-MS (ESI POS): 245.1 (MH+)—OH |
| 22 | 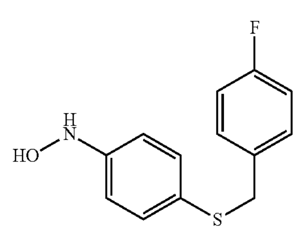 [SMILES: ONc1ccc(SCc2ccc(F)cc2)cc1] | LC-MS (ESI POS): 233.0 (MH+)—OH |

TABLE 3-continued

| Intermediate | Structure | Analytical |
|---|---|---|
| 23 | 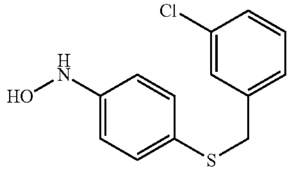 [SMILES: ONc1ccc(SCc2cccc(Cl)c2)cc1] | LC-MS (ESI POS): 266.0 (MH+) |

Example 5

Preparation of N-(biphenyl-4-yl)hydroxylamine (Intermediate 24)

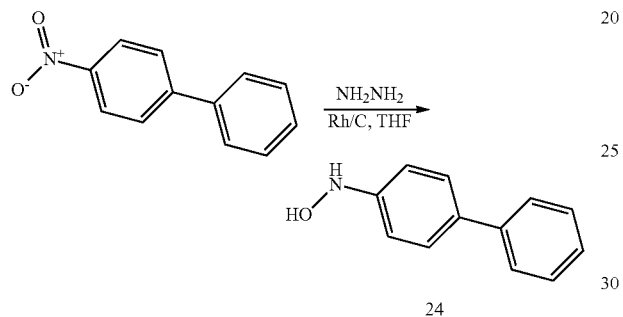

To a mixture of 4-nitrobiphenyl (400 mg, 2.008 mmol) and 5% rhodium on carbon (15 mg, 0.146 mmol) in tetrahydrofuran (15 ml), hydrazine hydrate (0.200 ml, 2.61 mmol) was added, and gas evolution was observed. The reaction mixture was stirred at RT for 25 minutes, then it was partitioned between diethyl ether (90 ml) and brine (20 ml), and the phases were separated. The aqueous phase was extracted with diethyl ether (90 ml), and the combined organic extracts were dried ($Na_2SO_4$) and concentrated to give 370 mg of the desired compound (89% purity) and about. The mixture was used as such for the next step.

LC-MS (ESI POS): 186.0 (MH+)

With an analogous procedure to that described in Example 5, the intermediates in Table 4 were obtained by reacting appropriate starting material.

TABLE 4

| Intermediate | Structure | Analytical |
|---|---|---|
| 25 | 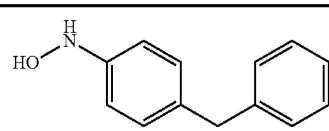 | LC-MS (ESI POS): 183.0 (MH+)—OH |
| 26 | 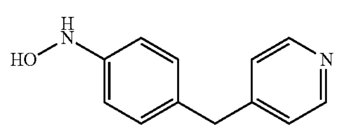 [SMILES: ONc1ccc(Cc2ccncc2)cc1] | LC-MS (ESI POS): 201.1 (MH+) |
| 27 | 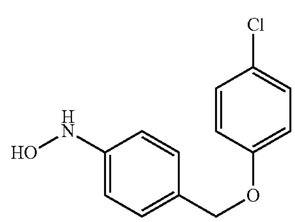 [SMILES: ONc1ccc(COc2ccc(Cl)cc2)cc1] | LC-MS (ESI POS): 232.0 (MH+)—$H_2O$ |
| 28 | 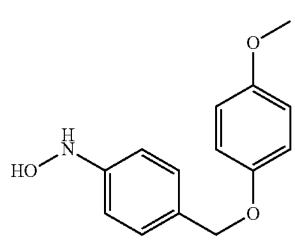 | LC-MS (ESI POS): 121.8 (MH+)-para-methoxyphenol |

TABLE 4-continued
| Intermediate | Structure | Analytical |
|---|---|---|
| 29 | 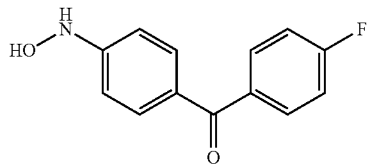 [SMILES: O=C(c1ccc(F)cc1)c1ccc(NO)cc1] | LC-MS (ESI POS): 232.1 (MH+) |
| 30 | 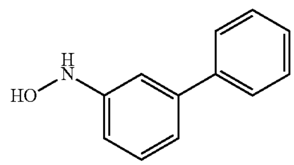 [SMILES: ONc1cccc(-c2ccccc2)c1] | LC-MS (ESI POS): 169.1 (MH+)—OH |
| 31 | 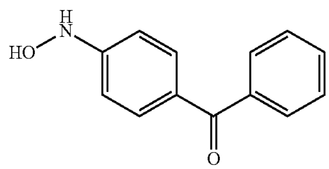 [SMILES: O=C(c1ccccc1)c1ccc(NO)cc1] | LC-MS (ESI POS): 214.0 (MH+) |
| 32 | 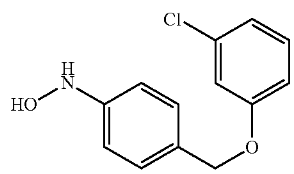 [SMILES: ONc1ccc(COc2cccc(Cl)c2)cc1] | LC-MS (ESI POS): 233.0 (MH+)—OH |
| 33 | 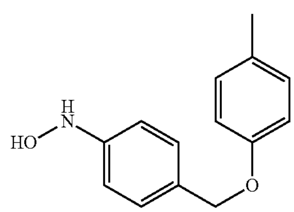 | LC-MS (ESI POS): 121.7 (MH+)-para-methylphenol |
Example 6
Preparation of (4aS,4bR,5S,6aS,6bR,9aS,10aS,10bS,12S)-4b,12-difluoro-8-[4-(4-fluoro-benzyloxy)-benzyl]-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one (Compound 6)
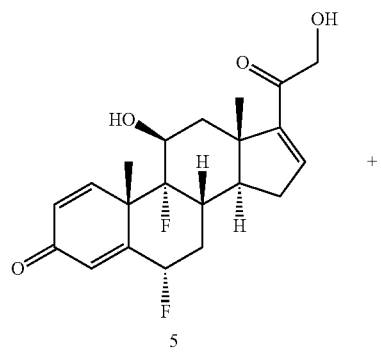
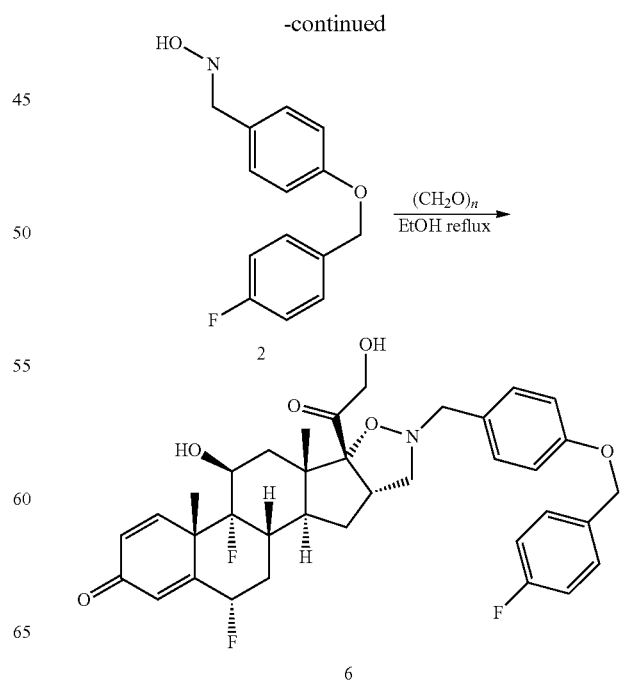

A mixture of intermediate 5 (600 mg, 1.586 mmol), crude N-(4-(4-fluorobenzyloxy)benzyl)hydroxylamine 2 (784 mg, 3.17 mmol) and paraformaldehyde (71.4 mg, 2.378 mmol) in ethanol (30 ml) was stirred at 105° C. for 24 hours. Further paraformaldehyde (47.6 mg, 1.586 mmol) was then added, and the mixture was stirred at 105° C. for further 6 hours. The solvent was evaporated and the residue was purified by flash chromatography on silica gel, in gradient elution from Petroleum ether/AcOEt 9:1 to Petroleum Ether/AcOEt 4:6, to afford the title compound 6 (813 mg, 1.275 mmol, 80% yield).

$^1$H NMR (300 MHz, DMSO-d$_6$) ppm 7.42-7.56 (m, 2 H), 7.26 (dd, 1 H), 7.12-7.24 (m, 4 H), 6.93 (m, 2 H), 6.30 (dd, 1 H), 6.12 (s, 1 H), 5.49-5.78 (m, 1H), 5.43 (dd, 1 H), 5.05 (s, 2 H), 4.66 (br. s., 1 H), 4.06-4.29 (m, 2 H), 3.92 (dd, 1 H), 3.81 (d, 1 H), 3.73 (d, 1 H), 3.31-3.54 (m, 2 H), 2.56-2.70 (m, 1 H), 2.01-2.33 (m, 3 H), 1.87-1.97 (m, 1 H), 1.51-1.71 (m, 3 H), 1.49 (s, 3 H), 1.42 (dd, 1H), 0.80 (s, 3 H)

LC-MS (ESI POS): 638.24 MH+

$[\alpha]_D^{25}$=+146.7 (c 0.36; CHCl$_3$)

The compounds listed in Table 5 were prepared with an analogous procedure as previously described for compound 6 in Example 6, by cycloaddition of intermediate 5 with suitable hydroxylamine or hydroxylamine hydrochloride as indicated.

TABLE 5

| Compound | Structure | Starting material Ref. | Analytical |
|---|---|---|---|
| 12 | 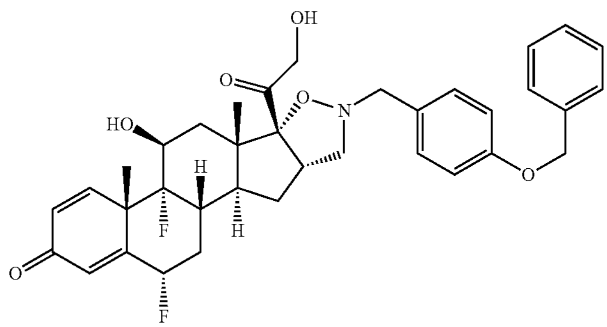 | Int. 11 | LC-MS (ESI POS): 620.2 MH+<br>$[\alpha]_D^{25}$ = +176 (c 0.3, MeOH)<br>$^1$H NMR (300 MHz, DMSO-d$_6$) ppm 7.30-7.54 (m, 5 H), 7.23-7.30 (m, 1 H), 7.19 (m, 2 H), 6.94 (m, 2 H), 6.30 (dd, 1 H), 6.13 (s, 1 H), 5.48-5.83 (m, 1 H), 5.43 (d, 1 H), 5.07 (s, 2 H), 4.51-4.78 (m, 1 H), 4.05-4.30 (m, 2 H), 3.93 (dd, 1 H), 3.77 (dd, 2 H), 3.32-3.48 (m, 2 H), 2.53-2.69 (m, 1 H), 1.99-2.35 (m, 3 H), 1.84-1.99 (m, 1 H), 1.36-1.71 (m, 4 H), 1.49 (s, 3 H), 0.80 (s, 3 H) |
| 34 | 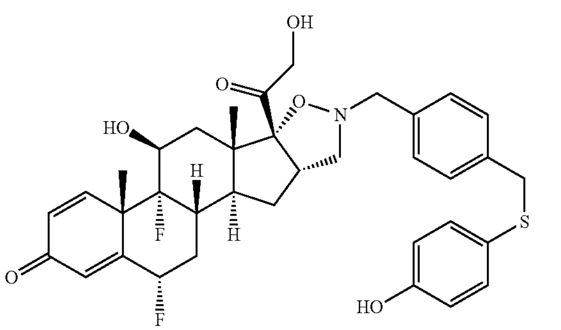 | Int. 17 | LC-MS (ESI POS): 652.3 MH+<br>$[\alpha]_D^{25}$ = +116.4 (c 0.52, MeOH)<br>$^1$H NMR (300 MHz, DMSO-d$_6$) ppm 9.50 (br. s., 1 H), 7.26 (dd, 1 H), 7.07-7.20 (m, 6 H), 6.61-6.73 (m, 2 H), 6.30 (dd, 1 H), 6.12 (s, 1 H), 5.48-5.74 (m, 1 H), 5.35-5.47 (m, 1 H), 4.51-4.78 (m, 1 H), 4.06-4.24 (m, 2 H), 4.00 (s, 2 H), 3.91 (d, 1 H), 3.84 (d, 1 H), 3.73 (d, 1 H), 3.33-3.54 (m, 2 H), 2.59-2.69 (m, 1 H), 2.00-2.32 (m, 3 H), 1.86-1.97 (m, 1 H), 1.51-1.69 (m, 3 H), 1.49 (s, 3 H), 1.35-1.47 (m, 1 H), 0.80 (s, 3 H) |
| 35 | 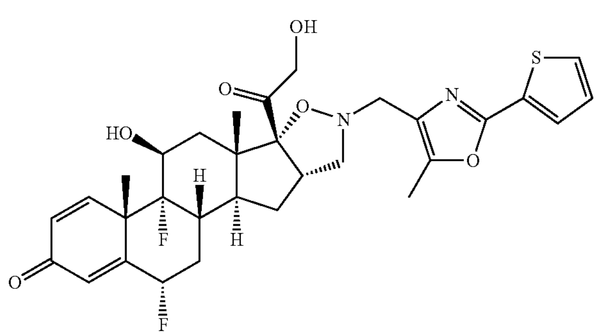 | Int. 18 | LC-MS (ESI POS): 601.2 MH+<br>$[\alpha]_D^{25}$ = +162.5 (C 0.16, MeOH)<br>$^1$H NMR (300 MHz, DMSO-d$_6$) ppm 7.71 (dd, 1 H), 7.59 (dd, 1 H), 7.26 (dd, 1 H), 7.17 (dd, 1 H), 6.30 (dd, 1 H), 6.11 (s, 1 H), 5.49-5.80 (m, 1 H), 5.44 (d, 1 H), 4.24 (d, 1 H), 4.11-4.20 (m, 1 H), 4.00 (d, 1 H), 3.79 (d, 1 H), 3.71 (d, 1 H), 3.23-3.49 (m, 2 H), 2.56-2.71 (m, 1 H), 2.33 (s, 3 H), 2.06-2.30 (m, 3 H), 1.84-2.00 (m, 1 H), 1.51-1.71 (m, 3 H), 1.49 (s, 3 H), 1.34-1.47 (m, 1 H), 0.81 (s, 3 H) |

Example 7

Preparation of (4aS,4bR,5S,6aS,6bR,9aS,10aS,10bS,12S)-4b,12-difluoro-8-[4-(4-fluoro-benzyloxy)-benzyl]-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid (Compound 7)

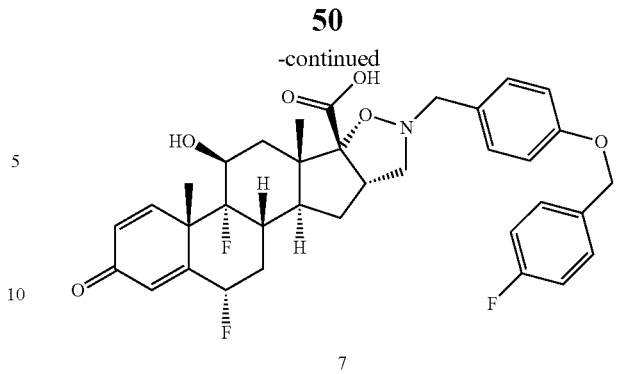

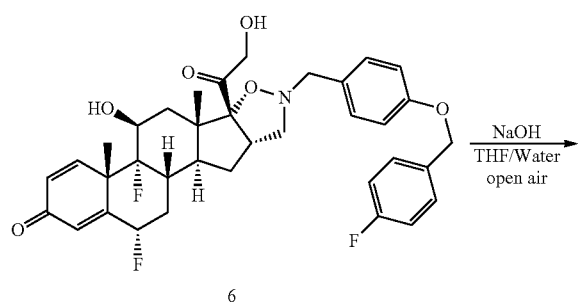

To a solution of 6 (660 mg, 1.035 mmol) in tetrahydrofuran (30 ml) and water (12 ml), at 0° C., air was bubbled for 15 minutes; then, 2 N sodium hydroxide (2.070 ml, 4.14 mmol) was slowly added dropwise, and air was bubbled for further 5 minutes at 0° C. The reaction mixture was left to warm up to RT and it was stirred at RT for 24 hours. The reaction mixture was acidified to pH 1 with 1 N HCl, and tetrahydrofuran was evaporated. The aqueous layer was extracted with AcOEt (100 ml×3). The combined organic extracts were washed with brine, dried ($Na_2SO_4$) and concentrated. The crude was triturated in petroleum ether, affording 642 mg of the title compound 7 (99%).

LC-MS (ESI POS): 624.1 (MH+)

With an analogous procedure to that described in Example 7, Compounds in Table 6 were obtained starting from appropriate starting material as indicated.

TABLE 6

| Compound | Structure | Starting material Ref. | Analytical |
|---|---|---|---|
| 13 | 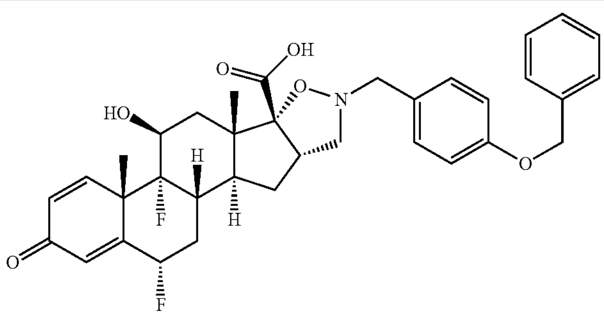 | Int. 12 | LC-MS (ESI POS): 606.2 MH+ |
| 51 | 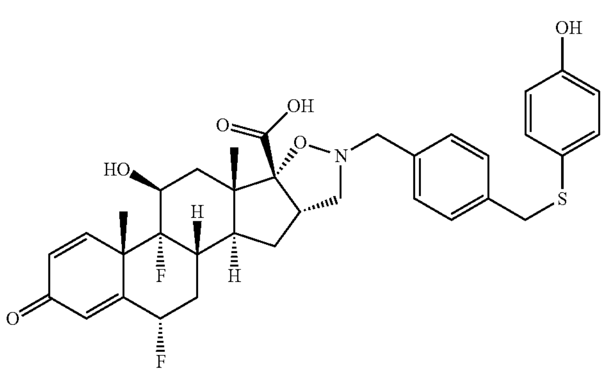 | Int. 34 | LC-MS (ESI POS): 638.20 MH+ |

Example 8

Preparation of (4aS,4bR,5S,6aS,6bR,9aS,10aS,10bS,12S)-8-((4-fluoro-benzyloxy)-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester (Compound 8)

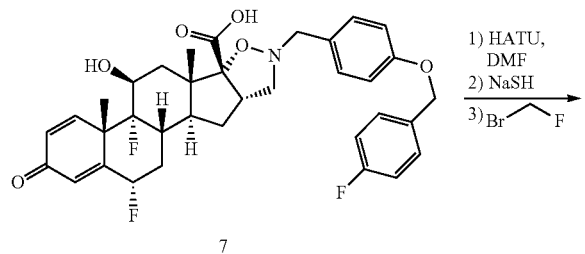

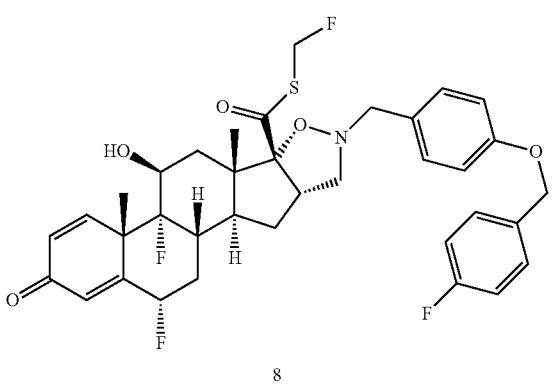

A mixture of compound 7 (620 mg, 0.994 mmol), HATU (378 mg, 0.994 mmol) and N-methylmorpholine (109 μl, 0.994 mmol) in dry DMF (15 ml) was stirred under nitrogen atmosphere at 70° C. for 30 minutes, and LC-MS showed the formation of the desired activated ester. The solution was cooled to RT, and anhydrous sodium hydrogen sulfide (58.3 mg, 1.040 mmol) was added. The mixture was stirred at RT for 30 minutes, then a 2 M solution of bromofluoromethane (746 μl, 1.491 mmol) in DMF was added, and the mixture was stirred at RT overnight. Water (50 ml) was added to the reaction mixture, and the formed precipitate was filtered. The collected precipitate was purified by flash chromatography on silica gel using as eluent acetone/petroleum ether 3:7. After evaporation of the solvent the residue was triturated with MeOH, filtered and dried under vacuum to afford 280 mg of the title compound 8 (41.9% yield).

$^1$H NMR (300 MHz, DMSO-$d_6$) ppm 7.39-7.58 (m, 2 H), 7.13-7.32 (m, 5H), 6.83-6.99 (m, 2 H), 6.30 (dd, 1 H), 6.12 (s, 1 H), 5.87 (dd, 1 H), 5.76 (dd, 1 H), 5.51-5.75 (m, 1 H), 5.49 (dd, 1 H), 5.04 (s, 2 H), 4.04-4.30 (m, 1 H), 3.89 (d, 1H), 3.83 (d, 1 H), 3.31-3.51 (m, 2 H), 2.56-2.70 (m, 1 H), 2.02-2.33 (m, 3 H), 1.83-1.95 (m, 1 H), 1.52-1.75 (m, 3 H), 1.49 (s, 3 H), 1.40-1.48 (m, 1 H), 0.88 (s, 3 H)

LC-MS (ESI POS): 672.19 (MH+)
$[\alpha]_D^{25}$=+122.9 (c 0.33; CHCl$_3$)

With an analogous procedure to that described in Example 8, Compounds of Table 7 were obtained starting from appropriate starting materials as indicated.

TABLE 7

| Compound | Structure | Starting material Ref | Analytical |
|---|---|---|---|
| 14 | 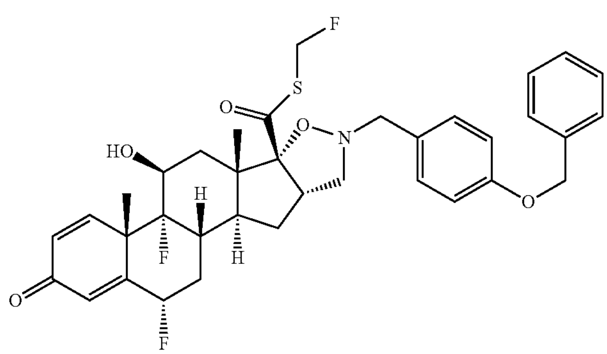 | Int. 13 | LC-MS (ESI POS): 654.12 MH+<br>$[\alpha]_D^{25}$ = +128.3 (c 0.37; CHCl$_3$)<br>$^1$H NMR (300 MHz, DMSO-$d_6$) ppm 7.28-7.48 (m, 5 H), 7.25 (dd, 1 H), 7.16-7.22 (m, 2 H), 6.87-6.99 (m, 2 H), 6.30 (dd, 1 H), 6.13 (s, 1 H), 5.87 (dd, 1 H), 5.76 (dd, 1 H), 5.51-5.74 (m, 1 H), 5.49 (dd, 1 H), 5.06 (s, 2 H), 4.05-4.27 (m, 1 H), 3.89 (d, 1 H), 3.83 (d, 1 H), 3.33-3.52 (m, 2 H), 2.56-2.69 (m, 1 H), 2.02-2.35 (m, 3 H), 1.82-1.97 (m, 1 H), 1.51-1.75 (m, 3 H), 1.49 (s, 3 H), 1.42-1.48 (m, 1 H), 0.89 (s, 3 H) |

TABLE 7-continued

| Compound | Structure | Starting material Ref | Analytical |
|---|---|---|---|
| 36 | 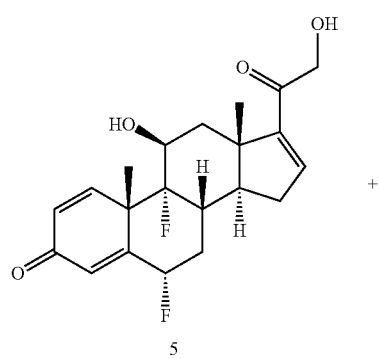 | Comp. 51 | LC-MS (ESI POS): 686.08 MH+<br>$[\alpha]_D^{25}$ = +120.8 (c 0.4, MeOH)<br>$^1$H NMR (300 MHz, DMSO-$d_6$) ppm 9.49 (s, 1 H), 7.24 (dd, 1 H), 7.12-7.16 (m, 2 H), 7.07-7.22 (m, 4 H), 6.53-6.81 (m, 2 H), 6.30 (dd, 1 H), 6.12 (s, 1 H), 5.87 (dd, 1 H), 5.76 (dd, 1 H), 5.52-5.76 (m, 1 H), 5.49 (dd, 1 H), 4.06-4.27 (m, 1 H), 3.99 (s, 2 H), 3.88 (s, 2 H), 3.33-3.53 (m, 2 H), 2.54-2.69 (m, 1 H), 2.08-2.34 (m, 3 H), 1.77-1.96 (m, 1 H), 1.49 (s, 3 H), 1.40-1.76 (m, 4 H), 0.88 (s, 3 H) |

Example 9

Preparation of 4aS,4bR,5S,6aS,6bR,9aS,10aS,10bS,12S)-4b,12-difluoro-5-hydroxy-6b-(2-hydroxy-acetyl)-4a,6a-dimethyl-8-[4-(4-hydroxy-phenylsulfanylmethyl)-phenyl]-4a,4b,5,6,6a,6b,8,9,9a,10,10a,10b,11,12-tetradecahydro-7-oxa-8-aza-pentaleno[2,1-a]phenanthren-2-one (Compound 37)

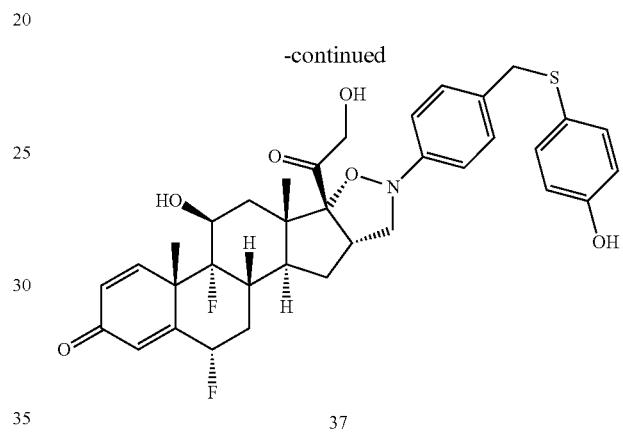

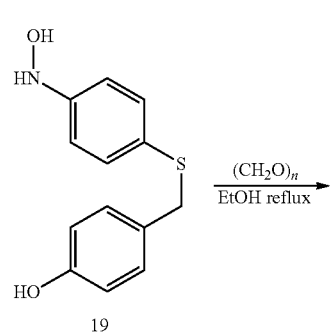

In a closed vessel, crude hydroxylamine 19 (597 mg, 2.414 mmol), 5 (457 mg, 1.207 mmol) and paraformaldehyde (109 mg, 3.62 mmol) were suspended in absolute ethanol (20 ml) and heated at 105° C. under microwaves irradiation for 1 hour and 30 minutes. The reaction mixture was concentrated, diluted with 9 mL of MeOH, and the mixture was directly purified by preparative HPLC (neutral phase) to yield the title compound (142 mg, 18.44% yield) as a pale yellow amorphous solid.

$^1$H NMR (300 MHz, DMSO-$d_6$) ppm 9.49 (br. s., 1 H), 7.26 (dd, 1 H), 7.05-7.20 (m, 4 H), 6.79-6.94 (m, 2 H), 6.60-6.76 (m, 2 H), 6.28 (dd, 1 H), 6.08 (s, 1H), 5.52-5.77 (m, 1 H), 5.51 (br. s., 1 H), 4.91 (br. s., 1 H), 4.47 (d, 1 H), 4.26 (d, 1H), 4.15-4.22 (m, 1 H), 4.08 (t, 1 H), 3.98 (s, 2 H), 3.50-3.64 (m, 1 H), 2.54-2.71 (m, 2 H), 1.97-2.34 (m, 3 H), 1.51-1.83 (m, 4 H), 1.49 (s, 3 H), 0.90 (s, 3 H)

LC-MS (ESI POS): 637.99 MH+
$[\alpha]_D^{25}$=+50.9 (c 0.31, MeOH)

With an analogous procedure to that described in Example 9, compounds of Table 8 were obtained starting from Intermediate 5 and appropriate starting materials as indicated.

TABLE 8

| Compound | Structure | Starting Material Ref | Analytical |
|---|---|---|---|
| 52 | (steroid structure with thiophene-phenyl substituent) | Int. 20 | LC-MS (ESI POS): 582.22 MH+<br>$[\alpha]_D^{25} = +12.6$ (c 0.4, CHCl$_3$)<br>$^1$H NMR (300 MHz, DMSO-d$_6$) ppm 7.52-7.62 (m, 2 H), 7.46 (dd, 1 H), 7.38 (dd, 1 H), 7.26 (dd, 1 H), 7.09 (dd, 1 H), 6.94-7.05 (m, 2 H), 6.28 (dd, 1 H), 6.08 (s, 1 H), 5.54-5.77 (m, 1 H), 5.52 (dd, 1 H), 4.95 (t, 1 H), 4.52 (dd, 1 H), 4.30 (dd, 1 H), 4.20-4.25 (m, 1 H), 4.16 (t, 1 H), 3.52-3.69 (m, 1 H), 2.55-2.71 (m, 2 H), 1.99-2.32 (m, 3 H), 1.62-1.89 (m, 2 H), 1.52-1.62 (m, 2 H), 1.50 (s, 3 H), 0.92 (s, 3 H) |
| 38 | (steroid structure with biphenyl substituent) | Int. 24 | LC-MS (ESI POS): 576.36 MH+<br>$[\alpha]_D^{25} = +71.90$ (c 0.158; CHCl$_3$)<br>$^1$H NMR (300 MHz, DMSO-d$_6$) ppm 7.59 (dd, 4 H), 7.43 (t, 2 H), 7.18-7.37 (m, 2 H), 7.07 (d, 2 H), 6.28 (dd, 1 H), 6.08 (s, 1 H), 5.43-5.79 (m, 1 H), 5.53 (d, 1 H), 4.95 (t, 1 H), 4.26-4.67 (m, 2 H), 4.13-4.26 (m, 2 H), 3.62 (q, 1 H), 2.63 (t, 2 H), 2.17-2.38 (m, 2 H), 2.11 (d, 1 H), 1.63-1.93 (m, 2 H), 1.50 (s, 3 H), 1.34-1.63 (m, 2 H), 0.92 (s, 3 H) |
| 39 | (steroid structure with phenyl-CH$_2$-S-methoxyphenyl substituent) | Int. 21 | LC-MS (ESI POS): 652.2 MH+<br>$[\alpha]_D^{25} = +73.2$ (c 0.21, MeOH)<br>$^1$H NMR (300 MHz, DMSO-d$_6$) ppm 7.21-7.36 (m, 3 H), 7.17 (d, 2 H), 6.79-6.99 (m, 4 H), 6.28 (dd, 1 H), 6.08 (s, 1 H), 5.38-5.76 (m, 1 H), 5.50 (d, 1 H), 4.90 (t, 1 H), 4.49 (dd, 1 H), 4.27 (dd, 1 H), 4.15-4.25 (m, 1 H), 4.04 (s, 2 H), 4.08 (t, 1 H), 3.72 (s, 3 H), 3.58 (q, 1 H), 2.54-2.71 (m, 2 H), 2.13-2.31 (m, 2 H), 2.06 (d, 1 H), 1.61-1.87 (m, 3 H), 1.49 (s, 3 H), 1.33-1.61 (m, 1 H), 0.90 (s, 3 H) |
| 40 | (steroid structure with benzylphenyl substituent) | Int. 25 | LC-MS (ESI POS): 590.31 MH+<br>$[\alpha]_D^{25} = +59$ (c 0.2, MeOH)<br>$^1$H NMR (300 MHz, DMSO-d$_6$) ppm 7.21-7.33 (m, 3 H), 7.07-7.21 (m, 5 H), 6.90 (d, 2 H), 6.28 (dd, 1 H), 6.08 (s, 1 H), 5.52-5.82 (m, 1 H), 5.50 (d, 1 H), 4.90 (t, 1 H), 4.50 (dd, 1 H), 4.27 (dd, 1 H), 4.19 (d, 1 H), 4.07 (t, 1 H), 3.86 (s, 2 H), 3.57 (q, 1 H), 2.64 (dd, 1 H), 2.56 (s, 1 H), 1.93-2.32 (m, 3 H), 1.59-1.90 (m, 2 H), 1.24-1.59 (m, 2 H), 1.49 (s, 3 H), 0.89 (s, 3 H) |

TABLE 8-continued

| Compound | Structure | Starting Material Ref | Analytical |
|---|---|---|---|
| 41 | 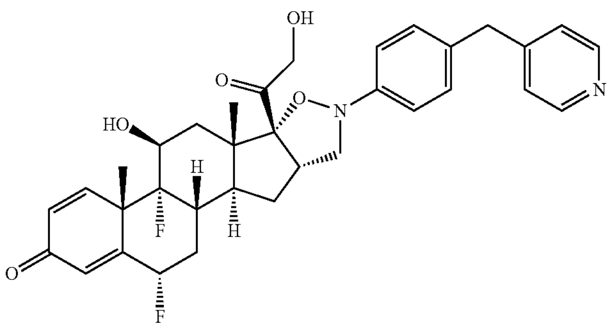 | Int. 26 | LC-MS (ESI POS): 591.24 MH+<br>$[\alpha]_D^{25} = +54.6$ (c 0.0985; MeOH)<br>$^1$H NMR (300 MHz, DMSO-d$_6$) ppm 8.25-8.50 (m, 2 H), 7.25 (dd, 1 H), 7.05-7.22 (m, 4 H), 6.82-6.98 (m, 2 H), 6.28 (dd, 1 H), 6.08 (s, 1 H), 5.52-5.81 (m, 1 H), 5.50 (dd, 1 H), 4.90 (t, 1 H), 4.49 (dd, 1 H), 4.27 (dd, 1 H), 4.14-4.22 (m, 1 H), 4.09 (t, 1 H), 3.89 (s, 2 H), 3.45-3.65 (m, 1 H), 2.60-2.72 (m, 1 H), 2.55 (dd, 1 H), 1.94-2.32 (m, 3 H), 1.70-1.86 (m, 1 H), 1.51-1.74 (m, 3 H), 1.49 (s, 3 H), 0.90 (s, 3 H) |
| 42 | 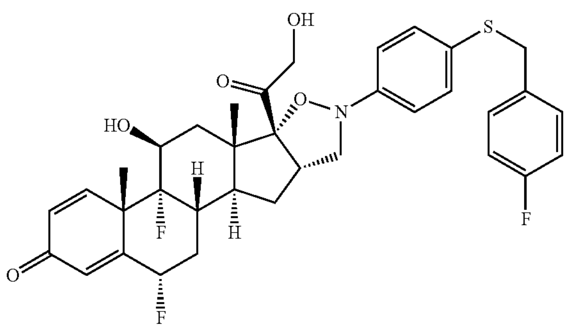 | Int. 22 | LC-MS (ESI POS): 640.13 MH+<br>$[\alpha]_D^{25} = +60.0$ (c 0.18 MeOH)<br>$^1$H NMR (300 MHz, DMSO-d$_6$) ppm 7.19-7.39 (m, 5 H), 6.99-7.16 (m, 2 H), 6.83-6.96 (m, 2 H), 6.28 (dd, 1 H), 6.08 (s, 1 H), 5.52-5.79 (m, 1 H), 5.51 (dd, 1 H), 4.93 (t, 1 H), 4.47 (dd, 1 H), 4.27 (dd, 1 H), 4.16-4.22 (m, 1 H), 4.11 (s, 2 H), 4.10 (t, 1 H), 3.49-3.68 (m, 1 H), 2.61-2.72 (m, 1 H), 2.56 (dd, 2 H), 1.93-2.35 (m, 3 H), 1.75 (d, 1 H), 1.60-1.72 (m, 1 H), 1.52-1.62 (m, 1 H), 1.49 (s, 3 H), 0.90 (s, 3 H) |
| 43 | 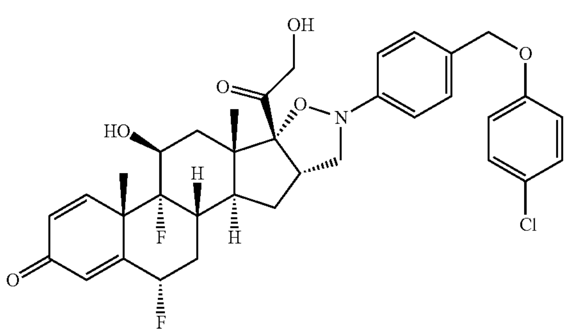 | Int. 27 | LC-MS (ESI POS): 640.13 MH+<br>$[\alpha]_D^{25} = +25.8$ (c 0.2 MeOH)<br>$^1$H NMR (300 MHz, DMSO-d$_6$) ppm 7.35 (d, 2 H), 7.31 (d, 2 H), 7.26 (dd, 1 H), 6.84-7.10 (m, 4 H), 6.28 (dd, 1 H), 6.08 (s, 1 H), 5.52-5.74 (m, 1 H), 5.50 (dd, 1 H), 5.01 (s, 2 H), 4.92 (t, 1 H), 4.50 (dd, 1 H), 4.29 (dd, 1 H), 4.17-4.24 (m, 1 H), 4.13 (t, 1 H), 3.59 (q, 1 H), 2.54-2.70 (m, 2 H), 1.99-2.25 (m, 3 H), 1.61-1.88 (m, 2 H), 1.37-1.61 (m, 2 H), 1.50 (s, 3 H), 0.91 (s, 3 H) |
| 44 | 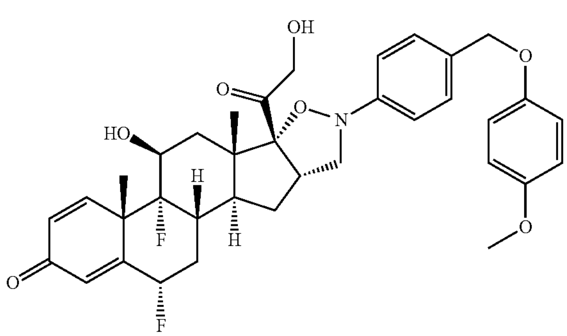 | Int. 28 | LC-MS (ESI POS): 636.18 MH+<br>$[\alpha]_D^{25} = +49.8$ (c 0.3; DCM)<br>$^1$H NMR (300 MHz, DMSO-d$_6$) ppm 7.34 (m, 2 H), 7.26 (dd, 1 H), 6.98 (m, 2 H), 6.75-6.94 (m, 4 H), 6.28 (dd, 1 H), 6.08 (s, 1 H), 5.51-5.77 (m, 1 H), 5.51 (d, 1 H), 4.94 (s, 2 H), 4.91 (t, 1 H), 4.50 (dd, 1 H), 4.29 (dd, 1 H), 4.21 (m, 1 H), 4.13 (t, 1 H), 3.68 (s, 3 H), 3.59 (q, 1 H), 2.54-2.70 (m, 2 H), 2.01-2.25 (m, 3 H), 1.50 (s, 3 H), 1.42-1.82 (m, 4 H), 0.91 (s, 3 H) |

TABLE 8-continued

| Compound | Structure | Starting Material Ref | Analytical |
|---|---|---|---|
| 45 | 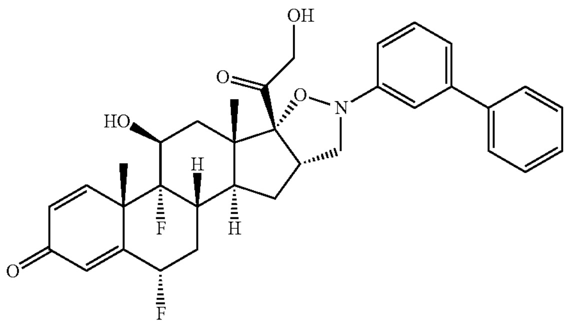 | Int. 30 | LC-MS (ESI POS): 576.33 MH+<br>$[\alpha]_D^{25}$ = +46.76 (c 0.071; MeOH)<br>$^1$H NMR (300 MHz, DMSO-d$_6$) ppm 7.58-7.66 (m, 2 H), 7.31-7.54 (m, 4 H), 7.22-7.31 (m, 2 H), 7.17 (t, 1 H), 6.88-7.06 (m, 1 H), 6.27 (dd, 1 H), 6.08 (s, 1 H), 5.54-5.76 (m, 1 H), 5.52 (dd, 1 H), 4.93 (t, 1 H), 4.55 (dd, 1 H), 4.32 (dd, 1 H), 4.17-4.24 (m, 1 H), 4.23 (t, 1 H), 3.52-3.68 (m, 1 H), 2.68 (dd, 1 H), 2.55-2.63 (m, 1 H), 2.04-2.31 (m, 3 H), 1.63-1.84 (m, 2 H), 1.52-1.64 (m, 2 H), 1.50 (s, 3 H), 0.92 (s, 3 H) |
| 46 | 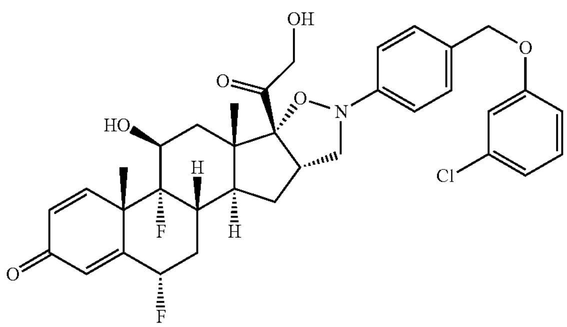 | Int. 32 | LC-MS (ESI POS): 640.21 MH+<br>$[\alpha]_D^{25}$ = +53.8 (c 0.26; MeOH)<br>$^1$H NMR (300 MHz, DMSO-d$_6$) ppm 7.33-7.43 (m, 2 H), 7.29 (t, 1 H), 7.26 (dd, 1 H), 7.07 (t, 1 H), 6.87-7.04 (m, 4 H), 6.28 (dd, 1 H), 6.08 (s, 1 H), 5.53-5.76 (m, 1 H), 5.51 (dd, 1 H), 5.04 (s, 2 H), 4.92 (t, 1 H), 4.50 (dd, 1 H), 4.29 (dd, 1 H), 4.17-4.24 (m, 1 H), 4.14 (t, 1 H), 3.50-3.71 (m, 1 H), 2.60-2.76 (m, 1 H), 2.59 (dd, 1 H), 2.02-2.32 (m, 3 H), 1.65-1.87 (m, 2 H), 1.51-1.68 (m, 2 H), 1.50 (s, 3 H), 0.91 (s, 3 H) |
| 47 | 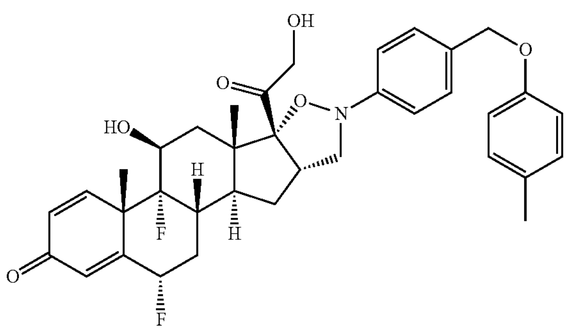 | Int. 33 | LC-MS (ESI POS): 620.4 MH+<br>$[\alpha]_D^{25}$ = +63 (c 0.1, MeOH)<br>$^1$H NMR (300 MHz, DMSO-d$_6$) ppm 7.30-7.43 (m, 2 H), 7.26 (dd, 1 H), 7.02-7.12 (m, 2 H), 6.93-7.02 (m, 2 H), 6.77-6.90 (m, 2 H), 6.28 (dd, 1 H), 6.08 (s, 1 H), 5.53-5.75 (m, 1 H), 5.51 (dd, 1 H), 4.97 (s, 2 H), 4.92 (t, 1 H), 4.50 (dd, 1 H), 4.29 (dd, 1 H), 4.17-4.24 (m, 1 H), 4.13 (t, 1 H), 3.50-3.68 (m, 1 H), 2.59-2.70 (m, 1 H), 2.58 (dd, 1 H), 2.21 (s, 3 H), 1.99-2.20 (m, 3 H), 1.63-1.84 (m, 2 H), 1.51-1.61 (m, 2 H), 1.50 (s, 3 H), 0.91 (s, 3 H) |
| 48 | 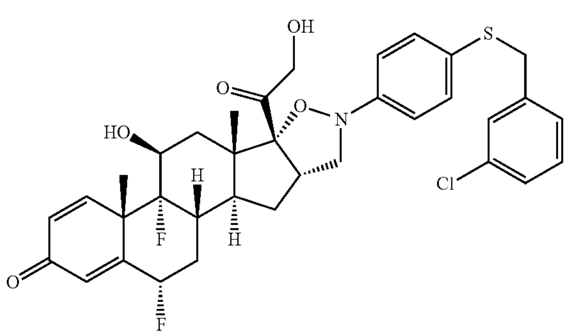 | Int. 23 | LC-MS (ESI POS): 656.21 MH+<br>$[\alpha]_D^{25}$ = +37.05 (c 0.21, MeOH)<br>$^1$H NMR (300 MHz, DMSO-d$_6$) ppm 7.10-7.39 (m, 7 H), 6.75-7.00 (m, 2 H), 6.28 (dd, 1 H), 6.08 (s, 1 H), 5.51-5.77 (m, 1 H), 5.43-5.52 (m, 1 H), 4.90 (t, 1 H), 4.47 (dd, 1 H), 4.27 (dd, 1 H), 4.15-4.21 (m, 1 H), 4.12 (s, 2 H), 4.05-4.11 (m, 1 H), 3.49-3.64 (m, 1 H), 2.57-2.71 (m, 2 H), 2.00-2.35 (m, 3 H), 1.51-1.81 (m, 4 H), 1.49 (s, 3 H), 0.90 (s, 3 H) |

Example 10

Preparation of (4aS,4bR,5S,6aS,6bR,9aS,10aS,10bS,12S)-4b,12-difluoro-5-hydroxy-8-[4-(4-hydroxy-phenylsulfanylmethyl)-phenyl]-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid (Compound 49)

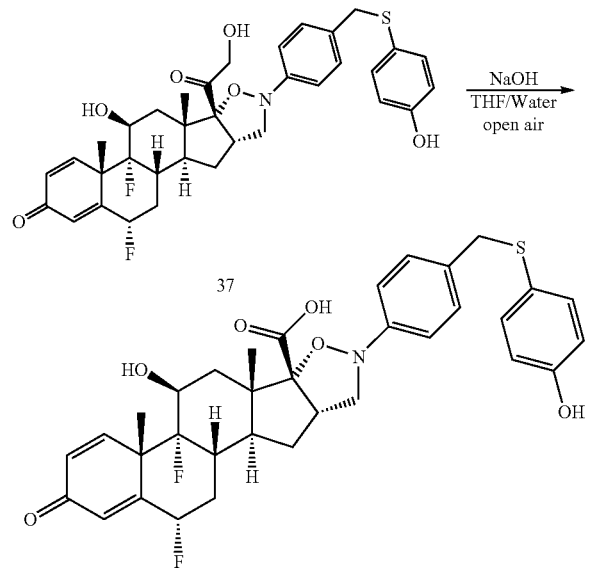

Compound 37 was dissolved in THF/water 3/1 mixture (28 mL). A 2 M solution of sodium hydroxide (1.678 ml, 3.36 mmol) was added, and the mixture was stirred for 24 hours at room temperature in an open vessel. 1N HCl was added until the pH was 5-6, and the reaction mixture was partitioned between water and AcOEt. The organic phase was separated, dried over $Na_2SO_4$ and concentrated to yield to give 590 mg of the desired compound 49 as a light yellow solid. The obtained product was used in the following step without further purification.

LC-MS (ESI POS): 624.75 (MH+)

Example 11

Preparation of (4aS,4bR,5S,6aS,6bR,9aS,10aS,10bS,12S)-4b,12-difluoro-5-hydroxy-4a,6a-dimethyl-8-[4-(4-hydroxy-phenylsulfanylmethyl)-phenyl]-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester (Compound 50)

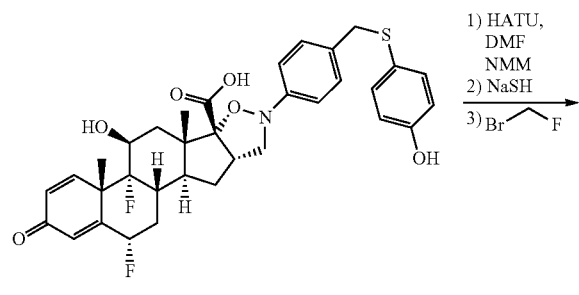

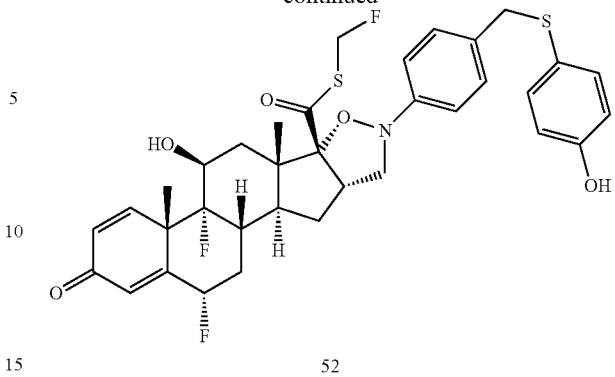

A mixture of acid 49 (523 mg, 0.839 mmol), HATU (351 mg, 0.923 mmol) and 4-methylmorpholine (93 mg, 0.923 mmol) in dry DMF (5 ml) was stirred at RT for 1.5 hours. Sodium hydrogensulfide (188 mg, 3.36 mmol) was added, and the mixture was stirred at RT for 45 minutes; then bromofluoromethane (95 mg, 0.839 mmol) was added and the solution was stirred at RT overnight. The mixture was partitioned between AcOEt and brine, and the organic phase was dried over $Na_2SO_4$ and concentrated. The crude was purified by preparative HPLC (neutral phase) to give compound 50 (71 mg, 12.60% yield) as pale yellow solid.

$^1$H NMR (300 MHz, DMSO-$d_6$) ppm 9.48 (s, 1 H), 7.24 (dd, 1 H), 7.10-7.20 (m, 4 H), 6.85-6.99 (m, 2 H), 6.60-6.74 (m, 2 H), 6.28 (dd, 1 H), 6.08 (s, 1H), 5.91 (dd, 1 H), 5.83 (dd, 1 H), 5.55 (dd, 1 H), 5.43-5.72 (m, 1 H), 4.16-4.28 (m, 1 H), 4.17 (t, 1 H), 3.99 (s, 2 H), 3.47-3.65 (m, 1 H), 2.56-2.71 (m, 2 H), 2.05-2.26 (m, 2 H), 1.94-2.05 (m, 1 H), 1.54-1.91 (m, 4 H), 1.49 (s, 3 H), 0.97 (s, 3H)

LC-MS (ESI POS): 672.21 (MH+)

$[\alpha]_D^{25}$=+51.8 (c 0.75, MeOH)

Pharmacological Activity of the Compounds of the Invention
In vitro Studies.

Example 12

Glucocorticoid Receptor (GR) Translocation Assay Protocol

A quantitative measurement of GR nuclear translocation of the compounds of the present invention may be performed according to ASSAY Drug Devel. Technol., 4(3), 263-272, 2006 (which is incorporated herein by reference in its entirety), through a novel cell-based GR-translocation assay in Enzyme Fragment Complementation (EFC) format developed by DiscoveRx (Fremont, Calif.). In the absence of the glucocorticoid, the glucocorticoid receptor (GR) resides in the cytosol complexed with a variety of proteins including heat shock proteins. When a glucocorticoid diffuses through the cell membrane into the cytoplasm and binds to the glucocorticoid receptor (GR), it results in release of the heat shock proteins and the translocation into the nucleus where it modulates gene transcription.

The DiscoveRx assay uses EFC of b-galactosidase (b-gal) as an indicator of GR-translocation in engineered CHO-K1 biosensor cells. The enzyme acceptor (EA) fragment of b-gal resides in the nucleus, as designed through the use of a proprietary set of sequence additions and modifications. The small peptide enzyme donor (ED) fragment of b-gal was fused directly to the C-terminus of GR, and was localized in the cytoplasm in the absence of receptor signaling. Upon binding to a GR ligand, the complex translocates to the nucleus, where intact enzyme activity was restored by complementation and b-gal activity was detected.

CHO-K1 cells stably expressing NLS-enzyme acceptor fragment (EA) of b-gal and GR-enzyme donor (ED) fragment of b-gal are maintained in F12 medium (Invitrogen, Carlsbad, Calif.) at 37° C. under a humidified atmosphere containing 5% $CO_2$ and 95% air. The medium contains 10% FBS, 2 mM L-glutamine, 50 U/ml penicillin 50 μg/ml streptomycin, and 250 μg/ml hygromycin and 500 μg/ml G418 (Invitrogen).

GR-translocation is measured using the PathHunter Detection Kit containing cell membrane permeabilizing reagent and beta-gal substrate (DiscoveRx, Fremont, Calif.). All compounds are screened using varying concentrations ranging from $10^{-11}$ to $10^{-6}$ M. The assay is performed in 48-wells (105 cells/well). Incubation with screened compounds is performed at 37° C. for two hours. Detection is made by adding the detection buffer from the kit supplied by DiscoveRx and incubating at room temperature for one hour. Luminescence is detected by using a CENTRO LB 960 microplate reader (Berthold Technologies).

Statistical analysis and determinations of EC50s are performed by using Prism-version 3.0 Graphpad Software (San Diego, Calif.).

Some representative Compounds of the invention resulted to display an EC50<10 nM when tested in the above described assay.

Example 13

Inhibition of LPS-Induced Nitric Oxide Production in RAW 264.7 Macrophages

An in vitro model based on macrophagic murine cell line RAW 264.7 may be used for testing the anti-inflammatory effects of the corticosteroids of the present invention.

During the inflammatory process, large amounts of nitric oxide (NO) are generated by the inducible isoforms of NO synthase (iNOS). Bacterial lipopolysaccharide (LPS) is commonly used in experimental settings to stimulate inflammatory responses in macrophages.

Cells are grown in a culture medium (RPMI supplemented with heat-inactivated 10% fetal calf serum, 2 mM glutamine, 100 U/ml penicillin and 0.1 mg/ml streptomycin) without phenol red. Cell stimulation is elicited by incubating cells for 24 hours with LPS to final concentrations ranging from 100 ng/ml. Treatments with the compounds of the invention are carried out by adding such compounds vehicled in DMSO (0.1% final concentration) to the final desired concentrations 15 minutes before LPS exposure. As an index of nitric oxide production, the concentration of nitrite is measured in the conditioned media by using the Griess colorimetric reaction (see *J. Neuroimmunol.*, 150, 29-36, 2004, which is incorporated herein by reference in its entirety).

Statistical analysis and determinations of IC50s are performed by using Prism-version 3.0 Graphpad Software (San Diego, Calif.).

Some representative Compounds of the invention resulted to display an IC50<10 nM when tested in the above described assay.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A compound of formula (I):

wherein
$R_1$ is $(CH_2)_n$—Z—$(CH_2)_{n'}$—$R_4$
n is 0, 1 or 2;
n' is 0, 1 or 2;
Z is a single bond or is selected from the group consisting of —S—, —O—, —C(O)—, and —$NR_3$;
$R_3$ is selected from the group consisting of H, ($C_1$-$C_6$)alkyl, ($C_1$-$C_6$)haloalkyl, ($C_3$-$C_8$)cycloalkyl, aryl, aryl($C_1$-$C_6$)alkyl, and heteroaryl, which are optionally substituted by —CN;
$R_4$ is selected from the group consisting of:
  H, halogen, —OH, —SH, —CN, and —$NR_6R_7$;
  aryl($C_1$-$C_6$)alkyl, ($C_1$-$C_6$)alkylsulfonyl, ($C_1$-$C_6$)alkylcarbonyl, ($C_1$-$C_6$)alkylcarboxyl, HO($C_1$-$C_6$)alkylcarboxyl, ($C_1$-$C_6$)alkylamide, and ($C_1$-$C_6$)alkoxy, which are optionally substituted by one or more oxo groups;
  ($C_1$-$C_6$)alkyl which may be optionally substituted by one or more substituents selected from the group consisting of a halogen atom, —CN, —OH, —$NH_2$, —$NO_2$, —$CF_3$, and —SH;
  ($C_2$-$C_6$)alkynyl;
  ($C_5$-$C_{17}$)alkenylcarbonyl; and
  a mono-, bi-, or tricyclic saturated or partially unsaturated or unsaturated ring, optionally substituted by one or more halogen atoms or oxo groups;
$R_6$ and $R_7$ are independently selected from the group consisting of H, ($C_1$-$C_6$)alkyl, and ($C_1$-$C_6$)alkoxy;
X and Y are independently H or halogen atoms;
$R_2$ is selected from the group consisting of: —$(CH_2)_s$—K-A-$(CH_2)_t$—W, —$(CH_2)_s$—K—$(CH_2)_t$—B—W, and —$(CH_2)_s$—$(CHR_5)$—W;
s is 0 or 1;
t is 0 or 1;
K is selected from the group consisting of a group —CH=CH—, arylene, and heteroarylene, where such arylene and heteroarylene groups may be optionally substituted by one or more groups independently selected from: halogen, ($C_1$-$C_6$)alkyl, —OH, ($C_1$-$C_6$)alkoxy, and ($C_1$-$C_6$)haloalkyl;
A is selected from the group consisting of a bond, —O—, and —S—;
B is selected from the group consisting of a bond, —O—, and —S—;
W is aryl or heteroaryl, where such aryl and heteroaryl groups may be optionally substituted by one or more groups independently selected from: halogen, —OH, (C$_1$-C$_6$)alkyl, (C$_1$-C$_6$)alkoxy, and (C$_1$-C$_6$)haloalkyl;

R$_5$ is aryl or heteroaryl, where such aryl and heteroaryl groups may be optionally substituted by one or more groups independently selected from halogen, (C$_1$-C$_6$) alkyl, (C$_1$-C$_6$)alkoxy, —OH, and (C$_1$-C$_6$)haloalkyl;

or a pharmaceutically acceptable salt thereof;

with the proviso that when s is 1, K is optionally substituted heteroarylene, t is zero, and A or B is a bond, then W is optionally substituted heteroaryl.

2. A compound or salt thereof according to claim 1 wherein stereogenic carbons have a stereochemistry as depicted in formula (I'):

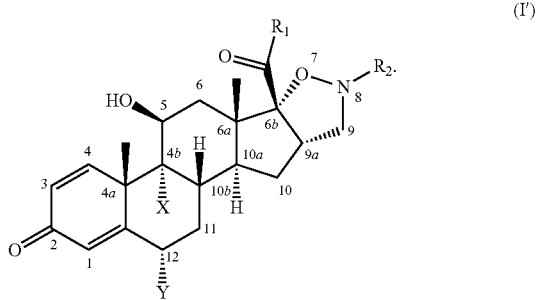

3. A compound or salt thereof according to claim 1, wherein X and Y are fluorine atoms.

4. A compound or salt thereof according to claim 1, wherein:
R$_1$ is —(CH$_2$)$_n$—Z—(CH$_2$)$_{n'}$—R$_4$, wherein n is 1, Z is a single bond, n' is 0 and R$_4$ is —OH; or
R$_1$ is —(CH$_2$)$_n$—Z—(CH$_2$)$_{n'}$—R$_4$, wherein n is 0, Z is —S—, n' is 1, and R$_4$ is a halogen atom; or
R$_1$ is —(CH$_2$)$_n$—Z—(CH$_2$)$_{n'}$—R$_4$, wherein n is 0, Z is a bond, n' is 1, and R$_4$ is a halogen atom.

5. A compound or salt thereof according to claim 1, wherein:
R$_2$ is —(CH$_2$)$_s$—K-A-(CH$_2$)$_t$—W or —(CH$_2$)$_s$—K—(CH$_2$)$_t$—B—W;
s is 0 or 1;
K is optionally substituted arylene or heteroarylene;
A is selected from the group consisting of a bond, —O—, and —S—;
B is selected from the group consisting of a bond, —O—, and —S—;
t is 0 or 1; and
W is optionally substituted aryl or heteroaryl.

6. A compound or salt thereof according to claim 1, wherein:
R$_2$ is —(CH$_2$)$_s$—K-A-(CH$_2$)$_t$—W or —(CH$_2$)$_s$—K—(CH$_2$)$_t$—B—W;
s is 1;
K is optionally substituted arylene or heteroarylene;
A is selected from the group consisting of a bond, —O—, and —S—;
B is selected from the group consisting of a bond, —O—, and —S—;
t is 0 or 1; and
W is optionally substituted aryl or heteroaryl.

7. A compound or salt thereof according to claim 1, wherein:
R$_2$ is —(CH$_2$)$_s$—K-A-(CH$_2$)$_t$—W or —(CH$_2$)$_s$—K—(CH$_2$)$_t$—B—W;
s is 0;
K is optionally substituted arylene or heteroarylene;
A is selected from the group consisting of a bond, —O—, and —S—;
B is selected from the group consisting of a bond, —O—, and —S—;
t is 0 or 1; and
W is optionally substituted aryl or heteroaryl.

8. A compound or salt thereof according to claim 1, which is:

(4aS,4bR,5S,6aS,6bR,9aS,10aS,10bS,12S)-4b,12-difluoro-8-[4-(4-fluoro-benzyloxy)-benzyl]-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-8-[4-(4-fluoro-benzyloxy)-benzyl]-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-8-((4-fluoro-benzyloxy)-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-8-(4-benzyloxy-benzyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-benzyloxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6bR,9aS,10aS,10bS,12S)-8-((S)-4-benzyloxy-benzyl)-4b,12-difluoro-5-hydroxy-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-6b-(2-hydroxy-acetyl)-4a,6a-dimethyl-8-[4-(4-hydroxy-phenylsulfanylmethyl)-benzyl]-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-[4-(4-hydroxy-phenylsulfanylmethyl)-phenyl]-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-4a,6a-dimethyl-8-[4-(4-hydroxy-phenylsulfanylmethyl)-benzyl]-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-6b-(2-hydroxy-acetyl)-4a,6a-dimethyl-8-(5-methyl-2-thiophen-2-yl-oxazol-4-ylmethyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-4a,6a-dimethyl-8-[4-(4-hydroxy-phenylsulfanylmethyl)-phenyl]-2-oxo-2,4a,4b,5,6,6a,8,9,9a,10,10a,10b,11,12-tetradecahydro-7-oxa-8-aza-pentaleno[2,1-a]phenanthrene-6b-carbothioic acid S-fluoromethyl ester;

(4aS,4bR,5S,6aS,6bR,9aS,10aS,10bS,12S)-4b,12-difluoro-5-hydroxy-6b-(2-hydroxy-acetyl)-4a,6a-dimethyl-8-(4-thiophen-2-yl-phenyl)4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-biphenyl-4-yl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-(4-methoxyphenylsulfanylmethyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-(4-benzyl-phenyl)-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-(4-pyridin-4-ylmethyl-phenyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-8-[4-(4-fluoro-benzylsulfanyl)-phenyl]-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-[4-(4-chloro-phenoxymethyl)-phenyl]-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-8-[4-(4-methoxy-phenoxymethyl)-phenyl]-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-biphenyl-3-yl-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-[4-(3-chloro-phenoxymethyl)-phenyl]-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-6b-(2-hydroxy-acetyl)-4a,6a-dimethyl-8-(3-p-tolyloxymethyl-phenyl)-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-8-[4-(3-chloro-benzylsulfanyl)-phenyl]-4b,12-difluoro-5-hydroxy-6b-(2-hydroxy-acetyl)-4a,6a-dimethyl-4a,4b,5,6,6a,6b,8,9,9a,10,10a,10b,11,12-tetradecahydro-7-oxa-8-aza-pentaleno[2,1-a]phenanthren-2-one;

(4aS,4bR,5S,6aS,6bR,9aS,10aS,10bS,12S)-4b,12-difluoro-5-hydroxy-8-[4-(4-hydroxy-phenylsulfanylmethyl)-phenyl]-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

(4aS,4bR,5S,6aS,6bR,9aS,10aS,10bS,12S)-4b,12-difluoro-5-hydroxy-8-[4-(4-hydroxy-phenylsulfanylmethyl)-benzyl]-4a,6a-dimethyl-2-oxo-2,4a,4b,5,6,6a,8,9,9a,10,10a,10b,11,12-tetradecahydro-7-oxa-8-aza-pentaleno[2,1-a]phenanthrene-6b-carboxylic acid;

or a pharmaceutically acceptable salt thereof.

9. A pharmaceutical composition, comprising a compound or a salt thereof according to claim 1 and one or more pharmaceutically acceptable carriers and/or excipients.

10. A combination, comprising a compound or salt thereof according to claim 1 and one or more active ingredients selected from the group consisting of a beta2-agonist, an antimuscarinic agent, a corticosteroid, a mitogen-activated protein kinase (P38 MAP kinase) inhibitor, a nuclear factor kappa-B kinase subunit beta (IKK2) inhibitor, a human neutrophil elastase (HNE) inhibitor, a phosphodiesterase 4 (PDE4) inhibitor, a leukotriene modulator, a non-steroidal anti-inflammatory agent (NSAID), and a mucus regulator.

11. A pharmaceutical composition, comprising a compound or a salt thereof according to claim 2 and one or more pharmaceutically acceptable carriers and/or excipients.

12. A pharmaceutical composition, comprising a compound or a salt thereof according to claim 3 and one or more pharmaceutically acceptable carriers and/or excipients.

13. A pharmaceutical composition, comprising a compound or a salt thereof according to claim 4 and one or more pharmaceutically acceptable carriers and/or excipients.

14. A pharmaceutical composition, comprising a compound or a salt thereof according to claim 5 and one or more pharmaceutically acceptable carriers and/or excipients.

15. A pharmaceutical composition, comprising a compound or a salt thereof according to claim 6 and one or more pharmaceutically acceptable carriers and/or excipients.

16. A method for the treatment of asthma or chronic obstructive pulmonary disease, said method comprising administering a therapeutically effective amount of a compound or salt thereof according to claim 1 to a patient in need thereof.

17. A method for the treatment of asthma or chronic obstructive pulmonary disease, said method comprising administering a therapeutically effective amount of a compound or salt thereof according to claim 2 to a patient in need thereof.

18. A method for the treatment of asthma or chronic obstructive pulmonary disease, said method comprising administering a therapeutically effective amount of a compound or salt thereof according to claim 3 to a patient in need thereof.

19. A method for the treatment of asthma or chronic obstructive pulmonary disease, said method comprising administering a therapeutically effective amount of a compound or salt thereof according to claim 4 to a patient in need thereof.

20. A method for the treatment of asthma or chronic obstructive pulmonary disease, said method comprising administering a therapeutically effective amount of a compound or salt thereof according to claim 5 to a patient in need thereof.

* * * * *